United States Patent
Shibasaki et al.

[11] Patent Number: 5,880,301
[45] Date of Patent: Mar. 9, 1999

[54] OPTICALLY ACTIVE BIDENTATE PHOSPHINE LIGAND PALLADIUM COMPLEX

[75] Inventors: Masakatsu Shibasaki; Mikiko Sodeoka, both of Tokyo; Kazuhiko Ohrai, Funabashi, all of Japan

[73] Assignee: Nissan Chemical Industries, Ltd., Tokyo, Japan

[21] Appl. No.: 894,520

[22] PCT Filed: Feb. 23, 1996

[86] PCT No.: PCT/JP96/00418

§ 371 Date: Sep. 16, 1997

§ 102(e) Date: Sep. 16, 1997

[87] PCT Pub. No.: WO96/26210

PCT Pub. Date: Aug. 29, 1996

[30] Foreign Application Priority Data

Feb. 24, 1995 [JP] Japan .................................. 7-036580
Oct. 31, 1995 [JP] Japan .................................. 7-282904

[51] Int. Cl.$^6$ .............................. C07F 9/02; C07F 15/00
[52] U.S. Cl. ............................ 556/21; 556/14; 556/136; 502/162; 548/402; 549/206; 549/430; 568/347; 568/349; 568/362
[58] Field of Search ................................. 556/21, 14, 136; 502/162; 548/402; 549/206, 430; 568/347, 349, 362

[56] References Cited

FOREIGN PATENT DOCUMENTS

| A 59-1684 | 1/1984 | Japan . |
| A 63-72625 | 4/1988 | Japan . |
| A 64-921 | 1/1989 | Japan . |
| A 2-4711 | 1/1990 | Japan . |
| A 3-90021 | 4/1991 | Japan . |
| A 5-202084 | 8/1993 | Japan . |
| A 6-40895 | 2/1994 | Japan . |

OTHER PUBLICATIONS

Ozawa, F. et al., "Palladium–Catalyzed Asymmetric Arylation of 2,3–Dihydrofuran with Phenyl Triflate. A Novel Asymmetric Catalysis Involving a Kinetic Resolution Process," *Organometallics*, v. 12, pp. 4188–4196, 1993.

Reetz, M.T. et al., "Rhodium–Diphosphine Complexes as Catalysts in Aldol Additions," *Tetrahedron Letters*, v. 28, n. 7, pp. 793–796, 1987.

(List continued on next page.)

*Primary Examiner*—Porfirio Nazario-Gonzalez
*Attorney, Agent, or Firm*—Oliff & Berridge, PLC

[57] ABSTRACT

The present invention provides a novel optically active bidentate phosphine ligand palladium complex of formula (I) or (II) which can be used for the preparation of optically active β-hydroxyketones:

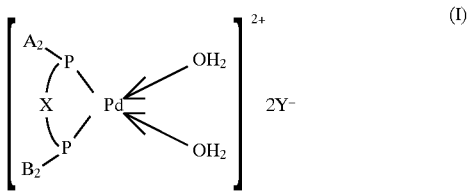

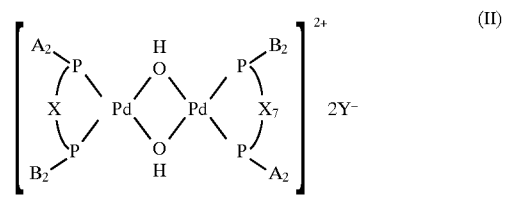

[wherein Y$^-$ represents an anion pair which may form salt; X represents

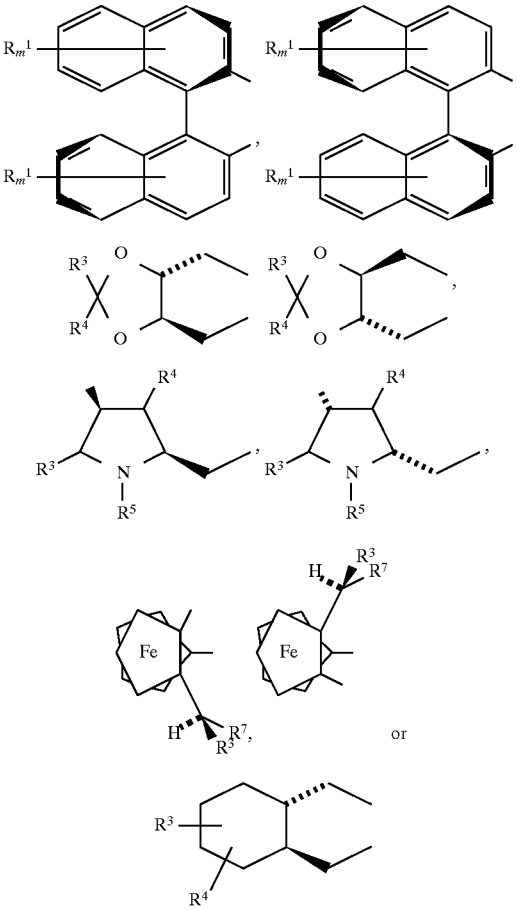

{wherein R$^1$ represents hydrogen atom, C$_{1-6}$ alkyl group, C$_{1-6}$ alkoxyl group, cyano group, nitro group, halogen atom or phenyl group, etc.; m represents 1 or 2; when m is 2, two R$^1$s may be same or different}; and A and B each independently represents phenyl group or cyclohexyl group {said phenyl group and cyclohexyl group each is unsubstituted or substituted by R$^2$ (R$^2$ has the same meaning as defined in R$^1$)}).

18 Claims, No Drawings

OTHER PUBLICATIONS

Heathcock, C.H. et al. *Comprehensive Organic Synthesis,* Pergamon Press: Oxford, v.2, ch. 1.5–1.9, 1991.

Heathcock, C.H., *Asymmetric Synthesis,* J.D. Morison, ed., Academic Press: New York, v.3, ch.2, 1984.

Roos, Gregory et al. "Enantioselective Approaches to Rhodium Catalysed Aldol–Type Reactions." *Synthetic Communications,* v. 23, n. 9, pp. 1251–1259, 1993.

Noyori, Ryoji. "BINAP: An Efficient Chiral Element for Asymmetric Catalysis." *Acc. Chem. Res.,* v23 pp. 345–350, 1990.

Hayashi, Tamio et al. "Asymmetric Catalytic Hydrosilylation of Ketones Preparation of Chiral Ferrocenylphosphines as Chiral Ligands." *Tetrahedron Letters,* No. 49–50, pp. 4405–4408, 1974.

Hayashi, Tamio et al. "Asymmetric Synthesis Catalyzed by Chiral Ferrocenylphsphine–Transition Metal Complexes. I. Preparation of Chiral Ferrocenylphophines." *Bull. Chem. Soc. Jpn.,* v53, pp. 1138–1151, 1980.

Hayashi, Teruyuki et al. "Catalytic Asymmetric Hydroformylation by the Use of Rhodium–complexes of Chiral Bidentate Phosphorus Ligands Bearing Saturated Ring Skeletons." *Bulletin of the Chemical Society of Japan,* v. 52, n. 9, pp. 2605–2608, 1970.

Achiwa, Kazuo. "Asymmetric Hydrogenation with New Chiral Functionalized Bisphospine–Rhodium Complexes." *Journal of the American Chemical Society,* v98, No. 25, pp. 8265–8266, Dec. 8, 1976.

Achiwa, Kazuo. "New Chiral Phosphine–Rhodium Catalysts for Asymmetric Synthesis of ®–and (S)–N–Benzyloxycarbonylalanine[1])." *Chemistry Letters,* pp. 777–778, 1977.

Ojima, Iwao et al. "N–Carbamoyl–4–Diphenylphosphino–2–Diphenylphophinomethlypyrrolidines (CAPP). Efficient New Chiral Ligands for Asymmetric Hydrogenation." *Tetrahedron Letters,* v. 21, pp. 1051–1054, 1980.

Murrer, Barry A. et al. "Synthesis of trans–4,5–Bis[diphenylarsinomethyl]–2,2–dimethyl–1,3–dioxolan and an Improved Preparation of its Phosphine Analogue (DIOP)." *Synthesis,* pp. 350–351, 1979.

Sodeoka, Mikiko et al. "Stable Diaqua Palladium (II) Complexes of BINAP and Tol–BINAP as Highly Efficient Catalysts for Asymmetric Aldol Reactions." *Synlett,* pp. 463–466, May 1997.

Hayashi, Tamio, et al., *Palladium–Catalyzed Asymmetric 1,4–Disilylation of α,β–Unsaturated Ketones: Catalytic Asymmetric Synthesis of β–Hydroxy Ketones,* Journal of the American Chemical Society, vol. 110, No. 16, pp. 5579–5581, 1988.

Matsumoto, Yonetatsu, et al., *Catalytic Asymmetric Synthesis of β–Hydroxy Ketones by Palladium–Catalyzed Asymmetric 1,4–Disilylation of α,β–Unsaturated Ketones,* Tetrahedron, vol. 50, No. 2, pp. 335–346, 1994.

OPTICALLY ACTIVE BIDENTATE PHOSPHINE LIGAND PALLADIUM COMPLEX

This application was filed as a request for U.S. examination under 35 U.S.C. § 371 of International application No. PCT/JP96/00418 filed Feb. 23, 1996.

TECHNICAL FIELD

The present invention relates to a novel optically active bidentate phosphine ligand palladium complex and the use thereof.

The novel optically active bidentate phosphine ligand palladium complex of the present invention may be used as a catalyst in the preparation of optically active β-hydroxyketones which are intermediates of medicines.

BACKGROUND ART

Recently, the organic synthesis reaction using a transition metal complex as a catalyst has been intensively developed, and especially, the asymmetric synthesis using an optically active bidentate phosphine ligand has been enthusiastically studied as a method of efficiently obtaining desired optically active substances. For instance, some reports disclose the development of the asymmetric catalyst using palladium as a transition metal, and there are known $Pd(BINAP)_2$ having the structure (A), (B) (Ozawa, F.; Kubo, A.; Matsumoto, Y.; Hayashi, T. *Organometallics,* 1993, 12, 4188), shown below, etc.; however, the palladium complex having the optically active bidentate phosphine as a ligand and coordinating with an water molecule or a hydroxyl group has not been known.

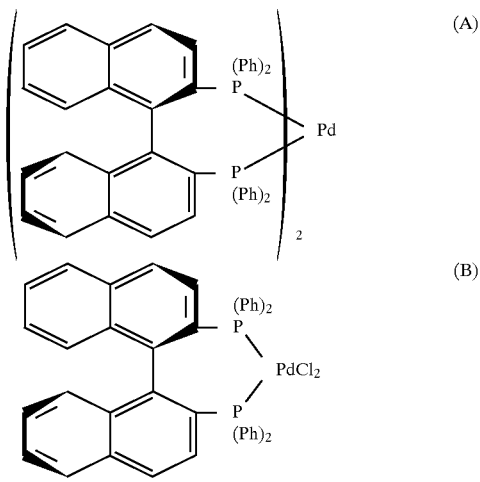

The catalytic asymmetric aldol reaction yielding an optically active β-hydroxyketone is the condensation reaction of silyl enol ether, ketene silylacetal or ketene silylthioacetal and an aldehyde with an optically active Lewis acid catalyst. The examples are described in the literatures such as (a) Heathcock, C. H., In Asymmetric Synthesis; Morison, J. D., Ed.; Academic press: New York:, 1984; Vol. 3, Chapter 2, (b) Heathcock, C. H., In Comprehensive Organic Synthesis; Perganon Press: Oxford, 1991; Vol. 2, Chapter 1.5–1.9, and the like. In the aldol reaction with these asymmetric Lewis acid catalysts, although extremely high asymmetric yields are reported, in view of the nature of the Lewis acid, the catalyst is expected to have an affinity for various oxygen-functional groups and the like in the preparation of medicines, and therefore, the application of such a reaction to complicated compounds is expected to have difficulty.

On the other hand, although the literatures such as Reetz, M. T.; Vougioukas, A. E., Tetrahedron Lett., 1987, 28, 793; Roos, G. H. P.; Haines, R. J.; Raab, C. E., Synth. Commun., 1993, 23, 1251, and the like disclose the catalytic asymmetric aldol reaction via a transition metal enolate which is not expected to have an affinity for various oxygen-functionnal groups and the like, yet the asymmetric yields are not much more than 20%, and hence the development of the transition metal complex having a novel optically active ligand and the efficient asymmetric synthesis using the complex has been desired. Since the asymmetric aldol reaction is applicable to the asymmetric synthesis of the aglycon of polyoxomacrolides such as erythromycin A, erythromycin B and the like, stereochemistry in the aldol reaction has been enthusiastically studied. The compound having a β-hydroxyketone as a moiety is exemplified by gingerol analogues. The gingerols are known as a compound which has cardiotonic activity (Japanese Patent Application Laid-open No. Sho 64-921 and Japanese Patent Application Laid-open No. Hei 6-40895), activity for platelet-aggregation (Japanese Patent Application Laid-open No. Sho 63-72625), analgesic activity (Japanese Patent Application No. Sho 59-1684), anti-inflammatory activity (Japanese Patent Application Laid-open No. Hei 3-90021), anti-parasitic activity (Japanese Patent Application Laid-open No. Hei 2-4711), and the like. Moreover, the mevalonic acid moiety of HMG-CoA reductase inhibitors has a β-hydroxyester, and therefore, a method of efficiently obtaining an optically active β-hydroxyketone is useful. However, the aldol reaction does not proceed and the β-hydroxyketone is not obtained even if the known complex of (A) or (B) is used.

DISCLOSURE OF THE INVENTION

The inventors intensively studied to solve the problems described above and has developed a novel optically active bidentate phosphine ligand palladium complex in which a water molecule or a hydroxyl group coordinates.

The complex is extremely useful as the catalyst of the aldol reaction.

Also, the inventors have found that the reaction is an entirely novel type reaction via a palladium enolate as an intermediate which is different from the known reaction using the asymmetric Lewis acid catalysts, and that the complex is useful as an asymmetric catalyst which gives high chemical and optical yields.

Furthermore, with respect to the optically active bidentate phosphine ligand used for synthesizing the palladium complex of the present invention, the two optically active substances may be prepared separately since the both enantiomers are easily available, and the inventors have established a novel optically active bidentate phosphine ligand palladium complex of which the stereo-structure is freely controlled and a novel reaction system which yields optically active β-hydroxyketones by using the complex to complete the present invention.

The present invention relates to an optically active bidentate phosphine ligand palladium complex and a method of synthesizing optically active β-hydroxyketones using the complex as the catalyst.

That is, the present invention relates to an optically active bidentate phosphine ligand palladium complex which is prepared from a palladium compound, an optically active bidentate phosphine ligand and silver salt, or from a palladium-optically active bidentate phosphine ligand complex and silver salt.

The optically active bidentate phosphine ligand palladium complex thus prepared is represented by the formula (I) or (II).

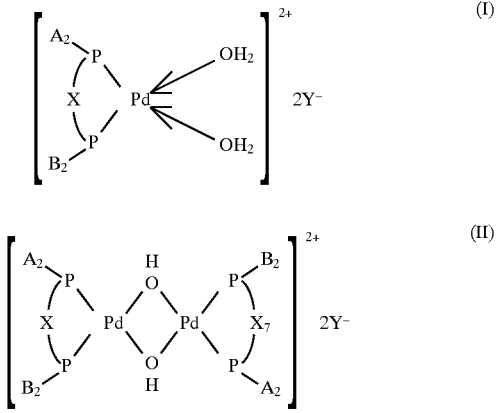

[wherein Y⁻ represents an anion pair which may form salt; X represents

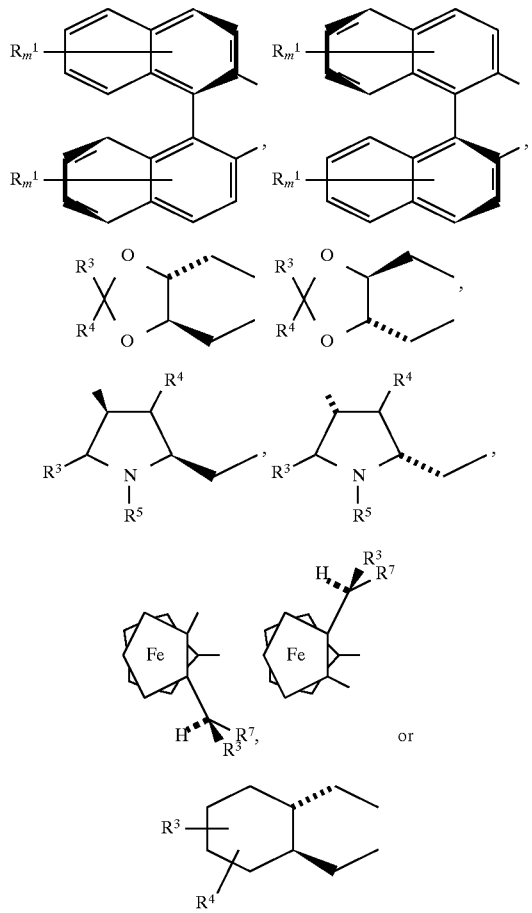

{where $R^1$ represents hydrogen atom, $C_{1-6}$ alkyl group, $C_{2-6}$ alkenyl group, $C_{2-6}$ alkynyl group, $C_{1-6}$ alkoxyl group (said alkyl group, alkenyl group, alkynyl group and alkoxyl group each is unsubstituted or substituted by halogen atom, hydroxyl group, tri($C_{1-6}$ alkyl)silyl group, $C_{1-6}$ alkyldiphenylsilyl group, di($C_{1-6}$ alkyl)phenylsilyl group, $C_{1-6}$ alkoxyl group, $C_{6-10}$ aromatic group or heterocyclic group), cyano group, nitro group, halogen atom or phenyl group (said phenyl group is unsubstituted or substituted by $C_{1-6}$ alkyl group, $C_{1-6}$ alkoxyl group, cyano group, nitro group or halogen atom);

$R^3$ and $R^4$ each independently represents $C_{1-6}$ alkyl group;

$R^5$ represents hydrogen atom, $COR^6$, $CO_2R^6$ or $CONHR^6$ ($R^6$ represents $C_{1-6}$ alkyl group);

$R^7$ represents hydroxyl group, $NR^4_2$ or $OCOR^4$;

m represents 1 or 2; when m is 2, two $R^1$s may be same or different}; and

A and B each independently represents phenyl group or cyclohexyl group {said phenyl group and cyclohexyl group are unsubstituted or substituted by $R^2$ ($R^2$ has the same meaning as defined in $R^1$)}]).

The present invention will be explained by referring to concrete examples of the substituents of the optically active bidentate phosphine ligand palladium complexes in the present specification.

In the present specification, "n" means normal, "i" means iso, "s" means secondary and "t" means tertiary.

As the $C_{1-6}$ alkyl group, methyl, ethyl, n-propyl, i-propyl, n-butyl, i-butyl, s-butyl, t-butyl, n-pentyl, i-pentyl, s-pentyl, neopentyl, 1-methylbutyl, 1,2-dimethylpropyl, n-hexyl, 1-methylpentyl and 2-ethylbutyl, etc. are mentioned.

As the $C_{2-6}$ alkenyl group, ethenyl, 1-propenyl, 2-propenyl, 1-methylvinyl, 1-butenyl, 2-butenyl, 3-butenyl, 1-methyl-1-propenyl, 1-methyl-2-propenyl, 2-methyl-2-propenyl, 1-ethyl-2-vinyl, 1-pentenyl, 2-pentenyl, 3-pentenyl, 4-pentenyl, 1,2-dimethyl-1-propenyl, 1,2-dimethyl-2-propenyl, 1-ethyl-1-propenyl, 1-ethyl-2-propenyl, 1-methyl-1-butenyl, 1-methyl-2-butenyl, 2-methyl-1-butenyl, 1-i-propylvinyl, 2,4-pentadienyl, 1-hexenyl, 2-hexenyl, 3-hexenyl, 4-hexenyl, 5-hexenyl, 2,4-hexadienyl, 1-methyl-1-pentenyl, etc. are mentioned.

As the $C_{2-6}$ alkynyl group, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, etc. are mentioned.

As the $C_{1-6}$ alkoxy group, methoxy, ethoxy, n-propoxy, i-propoxy, n-butoxy, i-butoxy, s-butoqxy, t-butoxy, n-pentyloxy, i-pentyloxy, s-pentyloxy, neopentyloxy, 1-methylbutoxy, 1,2-dimethylpropoxy, n-hexyloxy, 1-methylpentyloxy, 2-ethylbutoxy, etc. are mentioned.

As the halogen atom, fluorine atom, chlorine atom, bromine atom and iodine atom are mentioned.

The tri($C_{1-6}$ alkyl)silyl group represents silyl groups which are tri-substituted by the above-mentioned $C_{1-6}$ alkyl group. Examples thereof are trimethylsilyl, triethylsilyl, tri-n-propylsilyl, tri-n-butylsilyl, tri-n-pentylsilyl, tri-n-hexylsilyl, etc. Of these, trimethylsilyl is preferable.

The $C_{1-6}$ alkyldiphenylsilyl group represents diphenylsilyl groups which are mono-substituted by the above-mentioned $C_{1-6}$ alkyl group. Examples thereof are methyldiphenylsilyl, ethyldiphenylsilyl, n-butylphenylsilyl, t-butyldiphenyl, etc. Of these, t-butyldiphenylsilyl is preferable.

The di($C_{1-6}$ alkyl)phenylsilyl group represents phenylsilyl groups which are di-substituted by the above-mentioned $C_{1-6}$ alkyl group. Examples thereof are dimethylphenylsilyl, diethylphenylsilyl, di-n-butylphenylsilyl, di-t-butylphenylsilyl, etc. Of these, dimethylphenylsilyl and di-t-butylphenylsilyl are preferable.

As the $C_{6-10}$ aromatic groups, for example, phenyl, 1-indenyl, 2-indenyl, 3-indenyl, 4-indenyl, 5-indenyl, 6-indenyl, 7-indenyl, 1-naphthyl, 2-naphthyl, 1-tetrahydronaphthyl, 2-tetrahydronaphthyl, 5-tetrahydronaphthyl, 6-tetrahydronaphthyl, etc. are mentioned. Of these, phenyl, 1-naphthyl, 2-naphthyl, 1-tetrahydronaphthyl and 2-tetrahydronaphthyl are preferable. The above-mentioned groups are unsubstituted or substituted by $C_{1-6}$ alkyl, halogen atom or hydroxyl group.

As the heterocycle group, aromatic heterocycle groups and non-aromatic heterocycle groups are mentioned.

As the aromatic heterocycle group, monocyclic heterocycle groups having 5- to 7-membered rings, and fused bicyclic heterocycle groups which have 8 to 10 constituting atoms are mentioned. These groups can contain 1 to 3 atoms of oxygen atom, nitrogen atom or sulfur atom solely or in combination.

As the non-aromatic heterocycle group, monocyclic heterocycle groups having 5- to 7-membered rings, and fused bicyclic heterocycle groups which have 6 to 10 constituting atoms are mentioned. These groups can contain 1 to 3 atoms of oxygen atom, nitrogen atom or sulfur atom solely or in combination.

As the aromatic heterocycle group, for example, 2-thienyl, 3-thienyl, 2-furyl, 3-furyl, 2-pyranyl, 3-pyranyl, 4-pyranyl, 2-benzofuranyl, 3-benzofuranyl, 4-benzofuranyl, 5-benzofuranyl, 6-benzofuranyl, 7-benzofuranyl, 1-isobenzofuranyl, 4-isobenzofuranyl, 5-isobenzofuranyl, 2-benzothienyl, 3-benzothienyl, 4-benzothienyl, 5-benzothienyl, 6-benzothienyl, 7-benzothienyl, 1-isobenzothienyl, 4-isobenzothienyl, 5-isobenzothienyl, 2-chromenyl, 3-chromenyl, 4-chromenyl, 5-chromenyl, 6-chromenyl, 7-chromenyl, 8-chromenyl, 1-pyrrolyl, 2-pyrrolyl, 3-pyrrolyl, 1-imidazolyl, 2-imidazolyl, 4-imidazolyl, 1-pyrazolyl, 3-pyrazolyl, 4-pyrazolyl, 2-thiazolyl, 4-thiazolyl, 5-thiazolyl, 3-isothiazolyl, 4-isothiazolyl, 5-isothiazolyl, 2-oxazolyl, 4-oxazolyl, 5-oxazolyl, 3-isoxazolyl, 4-isoxazolyl, 5-isoxazolyl, 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, 1-indolizinyl, 2-indolizinyl, 3-indolizinyl, 5-indolizinyl, 6-indolizinyl, 7-indolizinyl, 8-indolizinyl, 1-isoindolyl, 4-isoindolyl, 5-isoindolyl, 1-indolyl, 2-indolyl, 3-indolyl, 4-indolyl, 5-indolyl, 6-indolyl, 7-indolyl, 1-indazolyl, 2-indazolyl, 3-indazolyl, 4-indazolyl, 5-indazolyl, 6-indazolyl, 7-indazolyl, 1-purinyl, 2-purinyl, 3-purinyl, 6-purinyl, 7-purinyl, 8-purinyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 1-phthalazinyl, 5-phthalazinyl, 6-phthalazinyl, 2-naphthyridinyl, 3-naphthyridinyl, 4-naphthyridinyl, 2-quinoxalinyl, 5-quinoxalinyl, 6-quinoxalinyl, 2-quinazolinyl, 4-quinazolinyl, 5-quinazolinyl, 6-quinazolinyl, 7-quinazolinyl, 8-quinazoliny, 3-cinnolinyl, 4-cinnolinyl, 5-cinnolinyl, 6-cinnolinyl, 7-cinnolinyl, 8-cinnolinyl, 2-pteridinyl, 4-pteridinyl, 6-pteridinyl, 7-pteridinyl, 3-furazanyl, etc. are mentioned.

As preferable aromatic heterocyclic ring groups are 2-thienyl, 3-thienyl, 2-furyl, 3-furyl, 2-pyranyl, 3-pyranyl, 4-pyranyl, 2-benzofuranyl, 3-benzofuranyl, 4-benzofuranyl, 5-benzofuranyl, 6-benzofuranyl, 7-benzofuranyl, 1-isobenzofuranyl, 4-isobenzofuranyl, 5-isobenzofuranyl, 2-benzothienyl, 3-benzothienyl, 4-benzothienyl, 5-benzothienyl, 6-benzothienyl, 7-benzothienyl, 1-isobenzothienyl, 4-isobenzothienyl, 5-isobenzothienyl, 2-chromenyl, 3-chromenyl, 4-chromenyl, 5-chromenyl, 6-chromenyl, 7-chromenyl, 8-chromenyl, 1-pyrrolyl, 2-pyrrolyl, 3-pyrrolyl, 1-imidazolyl, 2-imidazolyl, 4-imidazolyl, 1-pyrazolyl, 3-pyrazolyl, 4-pyrazolyl, 2-thiazolyl, 4-thiazolyl, 5-thiazolyl, 3-isothiazolyl, 4-isothiazolyl, 5-isothiazolyl, 2-oxazolyl, 4-oxazolyl, 5-oxazolyl, 3-isoxazolyl, 4-isoxazolyl, 5-isoxazolyl, 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, 1-indolizinyl, 2-indolizinyl, 3-indolizinyl, 5-indolizinyl, 6-indolizinyl, 7-indolizinyl, 8-indolizinyl, 1-isoindolyl, 4-isoindolyl, 5-isoindolyl, 1-indolyl, 2-indolyl, 3-indolyl, 4-indolyl, 5-indolyl, 6-indolyl and 7-indolyl.

As the non-aromatic heterocycle group, for example, 1-pyrrolidinyl, 2-pyrrolidinyl, 3-pyrrolidinyl, 1-pyrrolinyl, 2-pyrrolinyl, 3-pyrrolinyl, 4-pyrrolinyl, 5-pyrrolinyl, 1-imidazolidinyl, 2-imidazolidinyl, 4-imidazolidinyl, 1-imidazolinyl, 2-imidazolinyl, 4-imidazolinyl, 1-pyrazolidinyl, 3-pyrazolidinyl, 4-pyrazolidinyl, l-pyrazolinyl, 2-pyrazolinyl, 3-pyrazolinyl, 4-pyrazolinyl, 5-pyrazolinyl, 1-piperidyl, 2-piperidyl, 3-piperidyl, 4-piperidyl, 1-piperazinyl, 2-piperazinyl, 3-piperazinyl, 1-indolinyl, 2-indolinyl, 3-indolinyl, 4-indolinyl, 5-indolinyl, 6-indolinyl, 7-indolinyl, 1-isoindolinyl, 2-isoindolinyl, 4-isoindolinyl, 5-isoindolinyl, 2-quinuclidinyl, 3-quinuclidinyl, 4-quinuclidinyl, 2-morpholinyl, 3-morpholinyl, 4-morpholinyl, 1-azetidinyl, 2-azetidinyl, 3-azetidinyl, 1-azetidinonyl, 3-azetidinonyl, 4-azetidinonyl, etc. are mentioned.

Preferable non-aromatic heterocycle groups are 1-pyrrolidinyl, 2-pyrrolidinyl, 3-pyrrolidinyl, 1-pyrrolinyl, 2-pyrrolinyl, 3-pyrrolinyl, 4-pyrrolinyl, 5-pyrrolinyl, 1-imidazolidinyl, 2-imidazolidinyl, 4-imidazolidinyl, 1-imidazolinyl, 2-imidazolinyl, 4-imidazolinyl, 1-pyrazolidinyl, 3-pyrazolidinyl, 4-pyrazolidinyl, 1-pyrazolinyl, 2-pyrazolinyl, 3-pyrazolinyl, 4-pyrazolinyl, 5-pyrazolinyl, 1-piperidyl, 2-piperidyl, 3-piperidyl, 4-piperidyl, 1-piperazinyl, 2-piperazinyl, 3-piperazinyl, 2-morpholinyl, 3-morpholinyl and 4-morpholinyl.

The followings are given to describe the preferred examples of the compound of the present invention.

(1)

An optically active bidentate phosphine ligand palladium complex represented by the formula (I) or (II), wherein Y⁻ represents $ClO_4^-$, $NO_3^-$, $CH_3COO^-$, $CF_3SO_3^-$, $BF_4^-$, $PF_6^-$ $CF_3CO_2^-$, $AgCO_3^-$ or $AgPO_4^-$.

(2)

The optically active bidentate phosphine ligand palladium complex as described above in (1), wherein $R^1$ and $R^2$ each independently represents hydrogen atom, $C_{1-6}$ alkyl group, $C_{2-6}$ alkynyl group, $C_{1-6}$ alkoxyl group (said alkyl group, alkynyl group and alkoxyl group each is unsubstituted or substituted by halogen atom, tri($C_{1-6}$ alkyl)silyl group, $C_{1-6}$ alkyldiphenylsilyl group, di($C_{1-6}$ alkyl)phenylsilyl group, $C_{1-6}$ alkoxyl group, $C_{6-10}$ aromatic group or heterocyclic group), cyano group, halogen atom or phenyl group (said phenyl group is unsubstituted or substituted by $C_{1-6}$ alkyl group, $C_{1-6}$ alkoxyl group, cyano group or halogen atom).

(3)

The optically active bidentate phosphine ligand palladium complex as described above in (2), wherein $R^1$ represents hydrogen atom.

(4)

The optically active bidentate phosphine ligand palladium complex as described above in (3), wherein X represents

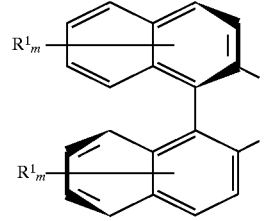

-continued

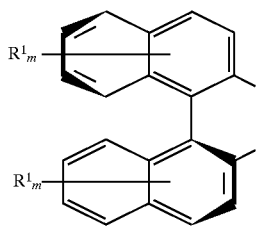

(5)
The optically active bidentate phosphine ligand palladium complex as described above in (4), wherein Y⁻ represents $ClO_4^-$, $CF_3SO_3^-$, $BF_4^-$ or $PF_6^-$.

(6)
The optically active bidentate phosphine ligand palladium complex as described above in (5), wherein $R^2$ represents hydrogen atom or $C_{1-6}$ alkyl group.

(7)
The optically active bidentate phosphine ligand palladium complex as described above in (6), wherein $R^2$ represents hydrogen atom or $C_{1-6}$ alkyl group and the number of $R^2$ is 3.

(8)
The optically active bidentate phosphine ligand palladium complex as described above in (7), wherein $R^2$ represents hydrogen atom, methyl group or methoxy group and the number of $R^2$ is 1.

(9)
The optically active bidentate phosphine ligand palladium complex as described above in (8), wherein $R^2$ represents methyl group or methoxy group, the number of $R^2$ is 1, and Y⁻ represents $BF_4^-$.

(10)
The optically active bidentate phosphine ligand palladium complex as described above in (8), wherein $R^2$ represents a hydrogen atom and Y⁻ represents $BF_4^-$.

The specific examples of the compound of the present invention are given below, but are not to be construed to limit the scope of the invention.

Me means methyl, Et means ethyl, Bu means butyl and Ph means phenyl.

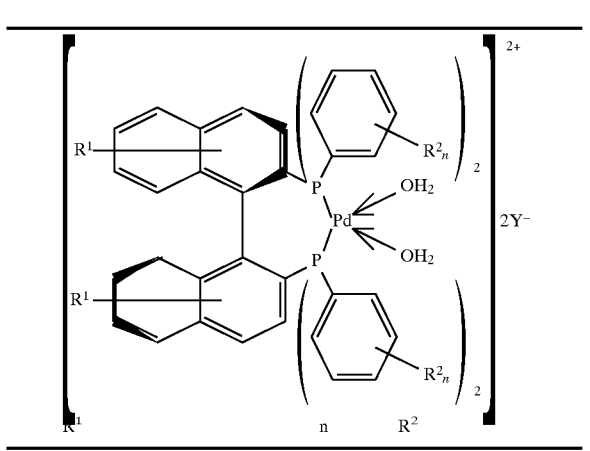

| R¹ | n | R² |
|---|---|---|
| H | — | H |
| 6,6'-Br | — | H |
| 6,6'-Me | — | H |
| 7,7'-Et | — | H |
| 6,6'-CN | — | H |
| 6,6-C≡CH | — | H |
| 6,6'-C≡CPh | — | H |
| 6,6'-C≡CSiMe₃ | — | H |
| 6,6'-C≡CSiEt₃ | — | H |
| 6,6'-C≡CSit—BuMe₂ | — | H |
| 7,7'-C≡CSiMe₂Ph | — | H |
| H | 1 | 2-Me |
| H | 1 | 4-Et |
| H | 1 | 2-t-Bu |
| H | 1 | 2-OMe |
| H | 1 | 3-OEt |
| H | 1 | 4-Ph |
| H | 3 | 2,3,4-Me₃ |
| H | 3 | 2,3,4-(OMe)₃ |

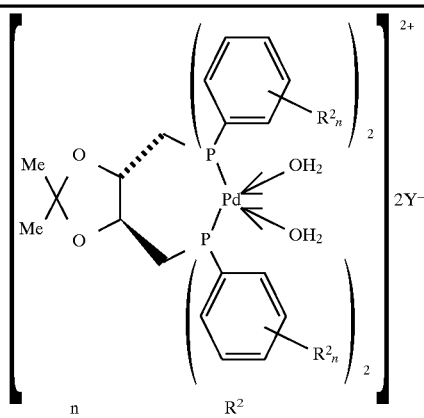

| n | R² |
|---|---|
| — | H |
| 1 | 2-Me |
| 1 | 4-Me |
| 1 | 2-t-Bu |
| 1 | 2-OMe |
| 1 | 4-OEt |
| 1 | 4-Ph |
| 2 | 3,5-(OMe)₂ |
| 3 | 3,4,5-Me₃ |
| 3 | 3,4,5-(OMe)₃ |

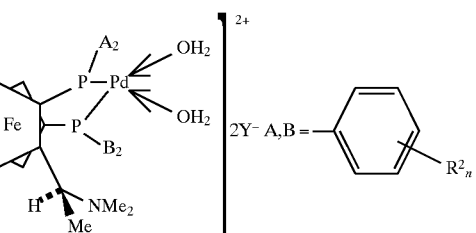

| n | R² |
|---|---|
| — | H |
| 1 | 2-Me |
| 1 | 4-Me |
| 1 | 2-t-Bu |
| 1 | 2-OMe |
| 1 | 4-OEt |
| 1 | 4-Ph |
| 2 | 3,5-(OMe)₂ |
| 3 | 3,4,5-Me₃ |
| 3 | 3,4,5-(OMe)₃ |

-continued

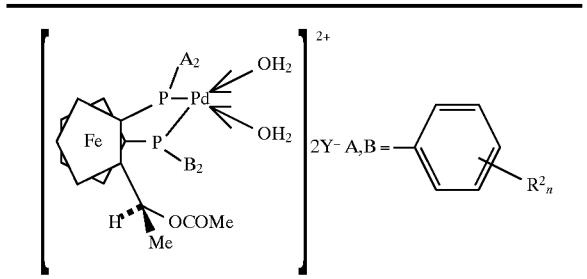

| n | R² |
|---|---|
| — | H |
| 1 | 2-Me |
| 1 | 4-Me |
| 1 | 2-t-Bu |
| 1 | 2-OMe |
| 1 | 4-OEt |
| 1 | 4-Ph |
| 2 | 3,5-(OMe)₂ |
| 3 | 3,4,5-Me₃ |
| 3 | 3,4,5-(OMe)₃ |

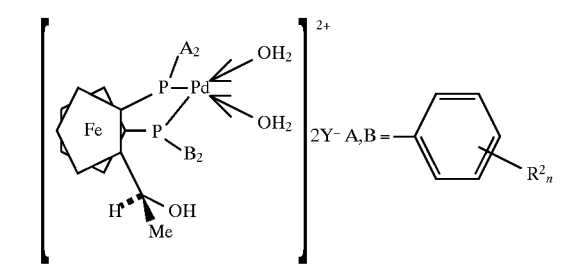

| n | R² |
|---|---|
| — | H |
| 1 | 2-Me |
| 1 | 4-Me |
| 1 | 2-t-Bu |
| 1 | 2-OMe |
| 1 | 4-OEt |
| 1 | 4-Ph |
| 2 | 3,5-(OMe)₂ |
| 3 | 3,4,5-Me₃ |
| 3 | 3,4,5-(OMe)₃ |

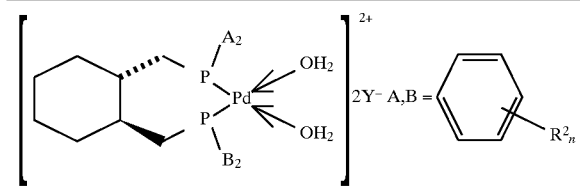

| n | R² |
|---|---|
| — | H |
| 1 | 2-Me |
| 1 | 4-Me |
| 1 | 2-t-Bu |
| 1 | 2-OMe |
| 1 | 4-OEt |
| 1 | 4-Ph |
| 2 | 3,5-(OMe)₂ |
| 3 | 3,4,5-Me₃ |
| 3 | 3,4,5-(OMe)₃ |

-continued

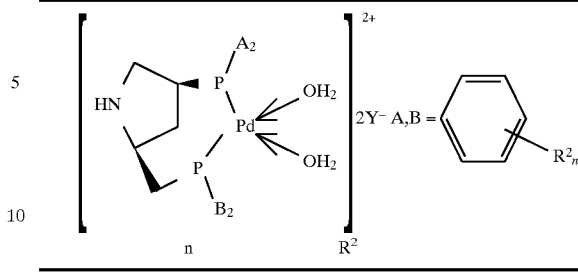

| n | R² |
|---|---|
| — | H |
| 1 | 2-Me |
| 1 | 4-Me |
| 1 | 2-t-Bu |
| 1 | 2-OMe |
| 1 | 4-OEt |
| 1 | 4-Ph |
| 2 | 3,5-(OMe)₂ |
| 3 | 3,4,5-Me₃ |
| 3 | 3,4,5-(OMe)₃ |

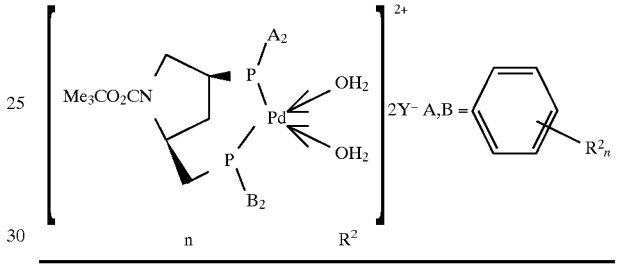

| n | R² |
|---|---|
| — | H |
| 1 | 2-Me |
| 1 | 4-Me |
| 1 | 2-t-Bu |
| 1 | 2-OMe |
| 1 | 4-OEt |
| 1 | 4-Ph |
| 2 | 3,5-(OMe)₂ |
| 3 | 3,4,5-Me₃ |
| 3 | 3,4,5-(OMe)₃ |

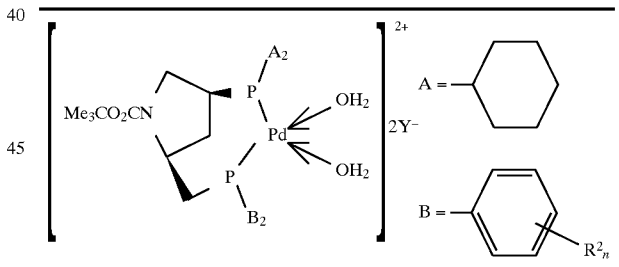

| n | R² |
|---|---|
| — | H |
| 1 | 2-Me |
| 1 | 4-Me |
| 1 | 2-t-Bu |
| 1 | 2-OMe |
| 1 | 4-OEt |
| 1 | 4-Ph |
| 2 | 3,5-(OMe)₂ |
| 3 | 3,4,5-Me₃ |
| 3 | 3,4,5-(OMe)₃ |

The optically active bidentate phosphine ligand palladium complex of the compound of the present invention may be used as the catalyst of the asymmetric aldol reaction which yields an optically active β-hydroxyketone as shown below.

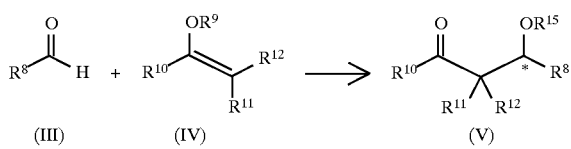

[wherein $R^8$ represents $C_{1-10}$ alkyl group, $C_{3-10}$ cycloalkyl group, $C_{2-10}$ alkenyl group, $C_{2-10}$ alkynyl group {said alkyl group, cycloalkyl group, alkenyl group and alkynyl group each is unsubstituted or substituted by halogen atom, hydroxyl group, $C_{1-10}$ alkoxyl group, $NR^{13}R^{13'}$ ($R^{13}$ and $R^{13'}$ each independently represents hydrogen atom, $C_{1-10}$ alkyl group or $C_{6-10}$ aromatic group, $SR^{14}$ ($R^{14}$ has the same meaning as definend in $R^{13}$), $C_{6-10}$ aromatic group or heterocyclic group}, $C_{6-10}$ aromatic group or heterocyclic group (said aromatic group and heterocyclic group each optionally has one to three and same or different substituents selected from the group consisting of $C_{1-10}$ alkyl group, $C_{1-10}$ alkoxyl group, halogen atom, nitro group, hydroxyl group, cyano group, $C_{1-10}$ alkoxycarbonyl group, $C_{1-10}$ alkanoyl group, amino group, N-mono($C_{1-10}$ alkyl)amino group, N,N-di($C_{1-10}$ alkyl)-amino group, carbamoyl group, N-mono($C_{1-10}$ alkyl)carbamoyl group, N,N-di($C_{1-10}$ alkyl) carbamoyl group, amino($C_{1-10}$ alkyl) group, N-mono($C_{1-10}$ alkyl)amino($C_{1-10}$ alkyl) group and N,N-di($C_{1-10}$ alkyl) amino($C_{1-10}$ alkyl) group);

$R^9$ represents substituted silyl group;

$R^{10}$ and $R^{11}$ each independently represents hydrogen atom, $C_{1-10}$ alkyl group, $C_{1-10}$ alkoxyl group, $C_{1-10}$ thioalkoxyl group, $C_{3-10}$ cycloalkyl group, $C_{2-10}$ alkenyl group, $C_{2-10}$ alkynyl group (said alkyl group, alkoxyl group, thioalkoxyl group, cycloalkyl group, alkenyl group and alkynyl group is unsubstituted or substituted by halogen atom, hydroxyl group, $C_{1-10}$ alkoxyl group, $NR^{13}R^{13'}$ ($R^{13}$ and $R^{13'}$ each independently represents as defined above), $SR^{14}$ ($R^{14}$ has the meaning as defined above), $C_{6-10}$ aromatic group or heterocyclic group}, $C_{6-10}$ aromatic group or heterocyclic group (said aromatic group and heterocyclic group each optionally has one to three same or different substituents selected from the group consisting of $C_{1-10}$ alkyl group, $C_{1-10}$ alkoxyl group, halogen atom, nitro group, hydroxyl group, cyano group, $C_{1-10}$ alkoxycarbonyl group, $C_{1-10}$ alkanoyl group, amino group, N-mono($C_{1-10}$ alkyl)amino group, N,N-di($C_{1-10}$ alkyl)amino group, carbamoyl group, N-mono($C_{1-10}$ alkyl)carbamoyl group, N,N-di($C_{1-10}$ alkyl)carbamoyl group, amino($C_{1-10}$ alkyl) group, N-mono($C_{1-10}$ alkyl)amino($C_{1-10}$ alkyl) group and N,N-di($C_{1-10}$ alkyl)amino($C_{1-10}$ alkyl) group); or $R^{10}$ and $R^{11}$, together with the carbon atom to which they are bound, represent a 5 to 7 membered carbocyclic group;

$R^{12}$ represents hydrogen atom, $C_{1-10}$ alkyl group (said alkyl group is unsubstituted or substituted by halogen atom, hydroxyl group or $C_{1-10}$ alkoxyl group); and $R^{15}$ represents hydrogen atom or substituted silyl group.

That is, the optically active bidentate phosphine ligand palladium complex of the compound of the present invention may be used as the catalyst in the preparation of the optically active β-hydroxyketones of the formula (V) by allowing the aldehyde of the formula (III) to react with the silyl enol ether of the formula (IV).

The specific examples of the substituent of the compound with respect to the preparation of the optically active β-hydroxyketones using the optically active bidentate phosphine ligand palladium complex of the present invention as the catalyst are given below.

As the $C_{1-10}$ alkyl group, methyl, ethyl, n-propyl, i-propyl, n-butyl, i-butyl, s-butyl, t-butyl, i-pentyl, 2-pentyl, 3-pentyl, i-pentyl, neopentyl, t-pentyl, 1-hexyl, 2-hexyl, 3-hexyl, 1-methyl-1-ethyl-n-pentyl, 1,1,2-trimethyl-n-propyl, 1,2,2-trimethyl-n-propyl, 3,3-dimethyl-n-butyl, 1-heptyl, 2-heptyl, 1-ethyl-1,2-dimethyl-n-propyl, 1-ethyl-2,2-dimethyl-n-propyl, 1-octyl, 3-octyl, 4-methyl-3-n-heptyl, 6-methyl-2-n-heptyl, 2-propyl-1-n-heptyl, 2,4,4-trimethyl-1-n-pentyl, 1-nonyl, 2-nonyl, 2,6-dimethyl-4-n-heptyl, 3-ethyl-2,2-dimethyl-3-n-pentyl, 3,5,5-trimethyl-1-n-hexyl, 1-decyl, 2-decyl, 4-decyl, 3,7-dimethyl-1-n-octyl, 3,7-dimethyl-3-n-octyl, etc. are mentioned. Of these, methyl, ethyl, n-propyl, i-propyl, n-butyl, i-butyl, s-butyl, t-butyl, i-pentyl, 1-hexyl, 1-heptyl, 1-octyl, 1-nonyl and 1-decyl are preferable.

As the $C_{3-10}$ cycloalkyl group, cyclopropyl, 1-methylcyclopropyl, 2-methylcyclopropyl, 4-methylcyclohexyl, cyclobutyl, cyclopentyl, cyclohexyl, cycloheptyl, cyclooctyl, cyclononyl, cyclodecyl, etc. are mentioned. Of these, cyclopropyl, cyclobutyl, cyclopentyl and cyclohexyl are preferable.

As the $C_{2-10}$ alkenyl group, ethenyl, 1-propenyl, 2-propenyl, 1-methylvinyl, 1-butenyl, 2-butenyl, 3-butenyl, 1-methyl-1-propenyl, 1-methyl-2-propenyl, 2-methyl-2-propenyl, 1-ethyl-2-vinyl, 1-pentenyl, 2-pentenyl, 3-pentenyl, 4-pentenyl, 1,2-dimethyl-1-propenyl, 1,2-dimethyl-2-propenyl, 1-ethyl-1-propenyl, 1-ethyl-2-propenyl, 1-methyl-1-butenyl, 1-methyl-2-butenyl, 2-methyl-1-butenyl, 1-i-propylvinyl, 2,4-pentadienyl, 1-hexenyl, 2-hexenyl, 3-hexenyl, 4-hexenyl, 5-hexenyl, 2,4-hexadienyl, 1-methyl-1-pentenyl, 1-heptenyl, 1-octenyl, 1-nonenyl, 1-decenyl, etc. are mentioned. Of these, ethenyl, 1-propenyl, 3-butenyl, 1-methyl-1-propenyl, 1-pentenyl, 4-pentenyl, 1-hexenyl, 5-hexenyl, 1-heptenyl, 1-octenyl, 1-nonenyl and 1-decenyl are preferable.

As the $C_{2-10}$ alkynyl group, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 1-octynyl, 1-nonynyl, 1-decynyl, etc. are mentioned. Of these, ethynyl, 1-propynyl, 1-butynyl, 1-pentynyl, 4-pentynyl, 1-hexynyl, 5-hexynyl, 1-heptynyl, 1-octynyl, 1-nonynyl and 1-decynyl are preferable.

As the halogen atom, fluorine atom, chlorine atom, bromine atom and iodine atom are mentioned.

As the $C_{1-10}$ alkoxy group, for example, methoxy, ethoxy, n-propoxy, i-propoxy, n-butoxy, sec-butoxy, t-butoxy, n-pentyloxy, n-hexyloxy, n-heptyloxy, n-octyloxy, n-nonyloxy, n-decyloxy, etc. are mentioned. Of these, methoxy, ethoxy, n-propoxy, i-propoxy, n-butoxy, sec-butoxy and t-butoxy are preferable.

As the $C_{6-10}$ aromatic groups, for example, phenyl, 1-indenyl, 2-indenyl, 3-indenyl, 4-indenyl, 5-indenyl, 6-indenyl, 7-indenyl, 1-naphthyl, 2-naphthyl, 1-tetrahydronaphthyl, 2-tetrahydronaphthyl, 5-tetrahydronaphthyl, 6-tetrahydronaphthyl, etc. are mentioned. Of these, phenyl, 1-naphthyl, 2-naphthyl, 1-tetrahydronaphthyl and 2-tetrahydronaphthyl are preferable.

As the heterocycle group, aromatic heterocycle groups and non-aromatic heterocycle groups are mentioned.

As the aromatic heterocycle group, monocyclic heterocycle groups having 5- to 7-membered rings, and fused bicyclic heterocycle groups which have 8 to 10 constituting atoms are mentioned. These groups can contain 1 to 3 atoms of oxygen atom, nitrogen atom or sulfur atom solely or in combination.

As the non-aromatic heterocycle group, monocyclic heterocycle groups having 5- to 7-membered rings, and fused bicyclic heterocycle groups which have 6 to 10 constituting atoms are mentioned. These groups can contain 1 to 3 atoms of oxygen atom, nitrogen atom or sulfur atom solely or in combination.

As the aromatic heterocycle group, for example, 2-thienyl, 3-thienyl, 2-furyl, 3-furyl, 2-pyranyl, 3-pyranyl, 4-pyranyl, 2-benzofuranyl, 3-benzofuranyl, 4-benzofuranyl, 5-benzofuranyl, 6-benzofuranyl, 7-benzofuranyl, 1-isobenzofuranyl, 4-isobenzofuranyl, 5-isobenzofuranyl, 2-benzothienyl, 3-benzothienyl, 4-benzothienyl, 5-benzothienyl, 6-benzothienyl, 7-benzothienyl, 1-isobenzothienyl, 4-isobenzothienyl, 5-isobenzothienyl, 2-chromenyl, 3-chromenyl, 4-chromenyl, 5-chromenyl, 6-chromenyl, 7-chromenyl, 8-chromenyl, 1-pyrrolyl, 2-pyrrolyl, 3-pyrrolyl, 1-imidazolyl, 2-imidazolyl, 4-imidazolyl, 1-pyrazolyl, 3-pyrazolyl, 4-pyrazolyl, 2-thiazolyl, 4-thiazolyl, 5-thiazolyl, 3-isothiazolyl, 4-isothiazolyl, 5-isothiazolyl, 2-oxazolyl, 4-oxazolyl, 5-oxazolyl, 3-isoxazolyl, 4-isoxazolyl, 5-isoxazolyl, 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, 1-indolizinyl, 2-indolizinyl, 3-indolizinyl, 5-indolizinyl, 6-indolizinyl, 7-indolizinyl, 8-indolizinyl, 1-isoindolyl, 4-isoindolyl, 5-isoindolyl, 1-indolyl, 2-indolyl, 3-indolyl, 4-indolyl, 5-indolyl, 6-indolyl, 7-indolyl, 1-indazolyl, 2-indazolyl, 3-indazolyl, 4-indazolyl, 5-indazolyl, 6-indazolyl, 7-indazolyl, 1-purinyl, 2-purinyl, 3-purinyl, 6-purinyl, 7-purinyl, 8-purinyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 1-phthalazinyl, 5-phthalazinyl, 6-phthalazinyl, 2-naphthyridinyl, 3-naphthyridinyl, 4-naphthyridinyl, 2-quinoxalinyl, 5-quinoxalinyl, 6-quinoxalinyl, 2-quinazolinyl, 4-quinazolinyl, 5-quinazolinyl, 6-quinazolinyl, 7-quinazolinyl, 8-quinazolinyl, 3-cinnolinyl, 4-cinnolinyl, 5-cinnolinyl, 6-cinnolinyl, 7-cinnolinyl, 8-cinnolinyl, 2-pteridinyl, 4-pteridinyl, 6-pteridinyl, 7-pteridinyl, 3-furazanyl, etc. are mentioned.

As preferable aromatic heterocycle groups are 2-thienyl, 3-thienyl, 2-furyl, 3-furyl, 2-pyranyl, 3-pyranyl, 4-pyranyl, 2-benzofuranyl, 3-benzofuranyl, 4-benzofuranyl, 5-benzofuranyl, 6-benzofuranyl, 7-benzofuranyl, 1-isobenzofuranyl, 4-isobenzofuranyl, 5-isobenzofuranyl, 2-benzothienyl, 3-benzothienyl, 4-benzothienyl, 5-benzothienyl, 6-benzothienyl, 7-benzothienyl, 1-isobenzothienyl, 4-isobenzothienyl, 5-isobenzothienyl, 2-chromenyl, 3-chromenyl, 4-chromenyl, 5-chromenyl, 6-chromenyl, 7-chromenyl, 8-chromenyl, 1-pyrrolyl, 2-pyrrolyl, 3-pyrrolyl, 1-imidazolyl, 2-imidazolyl, 4-imidazolyl, 1-pyrazolyl, 3-pyrazolyl, 4-pyrazolyl, *2-thiazolyl, 4-thiazolyl, 5-thiazolyl, 3-isothiazolyl, 4-isothiazolyl, 5-isothiazolyl, 2-oxazolyl, 4-oxazolyl, 5-oxazolyl, 3-isoxazolyl, 4-isoxazolyl, 5-isoxazolyl, 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, 1-indolizinyl, 2-indolizinyl, 3-indolizinyl, 5-indolizinyl, 6-indolizinyl, 7-indolizinyl, 8-indolizinyl, 1-isoindolyl, 4-isoindolyl, 5-isoindolyl, 1-indolyl, 2-indolyl, 3-indolyl, 4-indolyl, 5-indolyl, 6-indolyl and 7-indolyl.

As the non-aromatic heterocycle group, for example, 1-pyrrolidinyl, 2-pyrrolidinyl, 3-pyrrolidinyl, 1-pyrrolinyl, 2-pyrrolinyl, 3-pyrrolinyl, 4-pyrrolinyl, 5-pyrrolinyl, 1-imidazolidinyl, 2-imidazolidinyl, 4-imidazolidinyl, 1-imidazolinyl, 2-imidazolinyl, 4-imidazolinyl, 1-pyrazolidinyl, 3-pyrazolidinyl, 4-pyrazolidinyl, 1-pyrazolinyl, 2-pyrazolinyl, 3-pyrazolinyl, 4-pyrazolinyl, 5-pyrazolinyl, 1-piperidyl, 2-piperidyl, 3-piperidyl, 4-piperidyl, 1-piperazinyl, 2-piperazinyl, 3-piperazinyl, 1-indolinyl, 2-indolinyl, 3-indolinyl, 4-indolinyl, 5-indolinyl, 6-indolinyl, 7-indolinyl, 1-isoindolinyl, 2-isoindolinyl, 4-isoindolinyl, 5-isoindolinyl, 2-quinuclidinyl, 3-quinuclidinyl, 4-quinuclidinyl, 2-morpholinyl, 3-morpholinyl, 4-morpholinyl, 1-azetidinyl, 2-azetidinyl, -3-azetidinyl, 1-azetidinonyl, 3-azetidinonyl, 4-azetidinonyl, etc. are mentioned.

Preferable non-aromatic heterocycle groups are 1-pyrrolidinyl, 2-pyrrolidinyl, 3-pyrrolidinyl, 1-pyrrolinyl, 2-pyrrolinyl, 3-pyrrolinyl, 4-pyrrolinyl, 5-pyrrolinyl, 1-imidazolidinyl, 2-imidazolidinyl, 4-imidazolidinyl, 1-imidazolinyl, 2-imidazolinyl, 4-imidazolinyl, 1-pyrazolidinyl, 3-pyrazolidinyl, 4-pyrazolidinyl, 1-pyrazolinyl, 2-pyrazolinyl, 3-pyrazolinyl, 4-pyrazolinyl, 5-pyrazolinyl, 1-piperidyl, 2-piperidyl, 3-piperidyl, 4-piperidyl, 1-piperazinyl, 2-piperazinyl, 3-piperazinyl, 2-morpholinyl, 3-morpholinyl and 4-morpholinyl.

As the $C_{1-10}$ thioalkoxy group, for example, methylthio, ethylthio, n-propylthio, i-propylthio, n-butylthio, sec-butylthio, t-butylthio, n-pentylthio, n-hexylthio, n-heptylthio, n-octylthio, n-nonylthio and n-decylthio are mentioned.

Of these, methylthio, ethylthio, n-propylthio, i-propylthio, n-butylthio, sec-butylthio and t-butylthio are preferable.

As the substituted silyl group, trichlorosilyl, methyldichlorosilyl, dimethylchlorosilyl, trimethylsilyl, triethylsilyl, triethoxysilyl, ethyldiethoxysilyl, ethyldiisopropoxysilyl, diethylethoxysilyl, dimethylmethoxysilyl, dimethylethoxysilyl, dimethoxymethylsilyl, dimethylisopropoxysilyl, t-butyldimethylsilyl, t-butyldiphenylsilyl, etc. are mentioned. Of these, trimethylsilyl, triethylsilyl, t-butyldimethylsilyl and t-butyldiphenylsilyl are preferable.

Preferred methods of preparing the optically active β-hydroxyketones of the present invention are given below.

(1)

A method of preparing the optically active β-hydroxyketones as described above, wherein $R^8$ represents $C_{1-10}$ alkyl group, $C_{3-10}$ cycloalkyl group {said alkyl group and cycloalkyl group each is unsubstituted or substituted by $C_{1-10}$ alkyl group, $C_{3-10}$ cycloalkyl group (said alkyl group and cycloalkyl group each is unsubstituted or substituted by halogen atom, hydroxyl group, $C_{1-10}$ alkoxyl group, $NR^{13}R^{13'}$ ($R^{13}$ and $R^{13'}$ each independently represents hydrogen atom, $C_{1-10}$ alkyl group or $C_{6-10}$ aromatic group), $SR^{14}$ ($R^{14}$ has the same meaning as defined in $R^{13}$), $C_{6-10}$ aromatic group or heterocyclic group}, $C_{6-10}$ aromatic group or heterocyclic group (said aromatic group and heterocyclic group each optionally has one to three and same or different substituents selected from the group consisting of $C_{1-10}$ alkyl group, $C_{1-10}$ alkoxyl group, halogen atom, nitro group, hydroxyl group, cyano group, $C_{1-10}$ alkoxycarbonyl group, $C_{1-10}$ alkanoyl group, amino group, N-mono($C_{1-10}$ alkyl)amino group, N,N-di($C_{1-10}$ alkyl)amino group, carbamoyl group, N-mono($C_{1-10}$ alkyl)carbamoyl group, N,N-di($C_{1-10}$ alkyl)carbamoyl group, amino($C_{1-10}$ alkyl) group, N-mono($C_{1-10}$ alkyl)amino($C_{1-10}$ alkyl) group and N,N-di ($C_{1-10}$ alkyl)amino($C_{1-10}$ alkyl) group).

(2)

The method of preparing the optically active β-hydroxyketones as described above in (1), wherein $R^{10}$ and $R^{11}$ each independently represents hydrogen atom, $C_{1-10}$ alkyl group, $C_{1-10}$ alkoxyl group, $C_{1-10}$ thioalkoxyl group, $C_{3-10}$ cycloalkyl group {said alkyl group, alkoxyl group, thioalkoxyl group and cycloalkyl group each is unsubstituted or substituted by halogen atom, hydroxyl group, $C_{1-10}$ alkoxyl group, $NR^{13}R^{13'}$ ($R^{13}$ and $R^{13'}$ each independently represents hydrogen atom, $C_{1-10}$ alkyl group or $C_{6-10}$ aromatic group), $SR^{14}$ ($R^{14}$ has the same meaning as defined in $R^{13}$), $C_{6-10}$ aromatic group or heterocyclic group}, $C_{6-10}$ aromatic group or heterocyclic group (said aromatic group and heterocyclic group each optionally has one to three and same or different substituents selected from the group consisting of $C_{1-10}$ alkyl group, $C_{1-10}$ alkoxyl group, halogen atom, nitro group, hydroxyl group, cyano group, $C_{1-10}$ alkoxycarbonyl group, $C_{1-10}$ alkanoyl group, amino group, N-mono($C_{1-10}$ alkyl)amino group, N,N-di($C_{1-10}$ alkyl) amino group, carbamoyl group, N-mono($C_{1-10}$ alkyl) carbamoyl group, N,N-di($C_{1-10}$ alkyl)carbamoyl group, amino($C_{1-10}$ alkyl) group, N-mono($C_{1-10}$ alkyl)amino($C_{1-10}$ alkyl) group and N,N-di($C_{1-10}$ alkyl)amino($C_{1-10}$ alkyl) group); or $R^{10}$ and $R^{11}$, together with the carbon atom to which they are bound, represent a 5 to 7 membered carbocyclic group.

(3)

The method of preparing the optically active β-hydroxyketones as described above in (2), wherein $R^9$ represents trimethylsilyl group, triethylsilyl group, t-butyldimethylsilyl group or t-butyldiphenylsilyl group.

The preparation of the optically active bidentate phosphine ligand palladium complex of the compounds of the present invention is given below.

PREPARATION 1

The compound of (I) of the present invention is prepared from a palladium compound, an optically active bidentate phosphine ligand and silver salt in a solvent containing water as shown below.

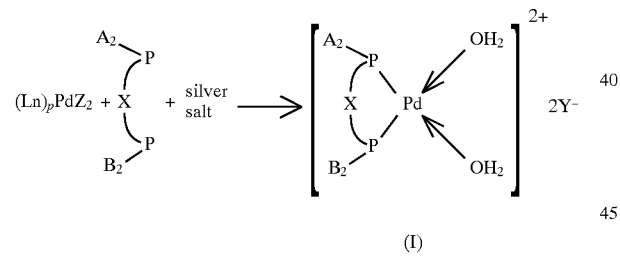

(I)

[wherein Ln represents a ligand which coordinates with the palladium, p represents an integer of from 0 to 2 which is the number of the ligands, and Z represents $OSO_2CF_3$ or halogen atom].

Instead of the compound of (I), the compound of (II) may be occasionally yielded depending upon the substituent of the compound. The compound of (II) may be also used for the use of the present invention.

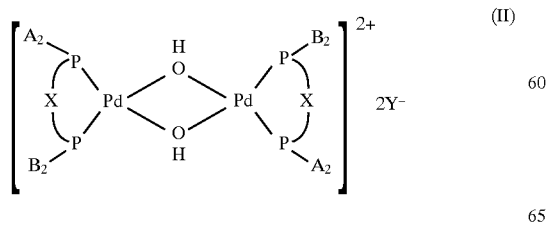

The palladium compound includes palladium chloride, palladium bromide, palladium iodide, dichlorobis (acetonitrile)palladium, dichlorobis(benzonitrile)palladium, dichlorobis(trimethylphosphine)palladium, dichlorobis(triphenylphosphine)palladium, dichlorobis(triethylphosphine)palladium, dichlorobis(tributylphosphine)palladium, dichlorobis(diphenylphosphinomethane)palladium, dichlorobis(diphenylphosphinoethane)palladium, dichlorobis(diphenylphosphinopropane)palladium and dichlorobis(diphenylphosphinobutane)palladium. Of these, palladium chloride, palladium bromide, palladium iodide, dichlorobis(acetonitrile)palladium and dichlorobis(benzonitrile) palladium are preferable.

The compound of the formula (C) as the optically active bidentate phosphine ligand may be available as a reagent or obtained by the known method (see, for instance, Acc. Chem. Res., 23, 345 (1990)). The compound of the formula (D) may be available as a reagent or obtained by the known method (see, for instance, Synthesis, 350 (1979)). The compound of the formula (E) may be available as a reagent or obtained by the known method (see, for instance, Tetrahedron Lett., 4405 (1974) and Bull. Chem. Soc. Jpn., 53, 1138 (1980)). The compound of the formula (F) may be available as a reagent or obtained by the known method (see, for instance, Bull. Chem. Soc. Jpn., 52, 2605 (1979)). The compound of the formula (G) may be available as a reagent or obtained by the known method (see, for instance, J. Am. Chem. Soc., 98, 8265 (1976), Chem. Lett., 777 (1977), and Tetrahedron Lett., 21, 1051 (1980)).

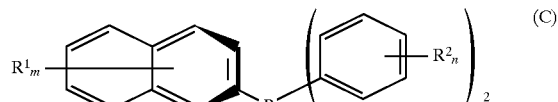
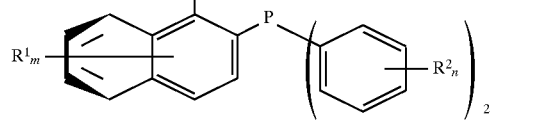
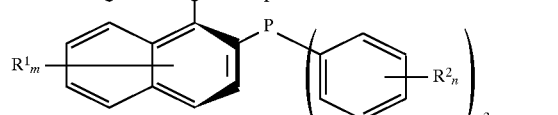

(C)

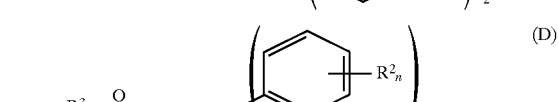
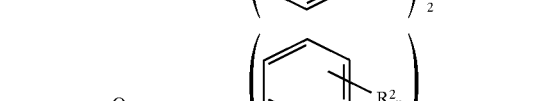
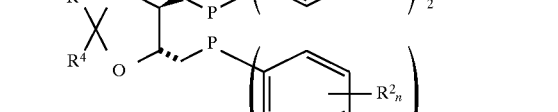

(D)

(E) 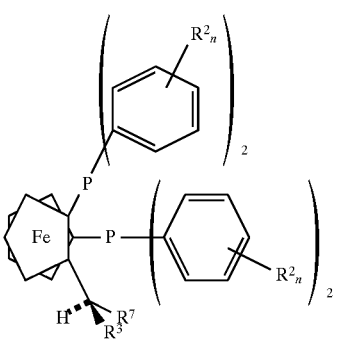

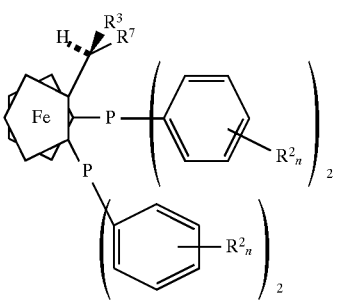

(F) 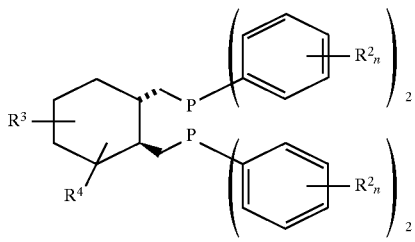

(G) 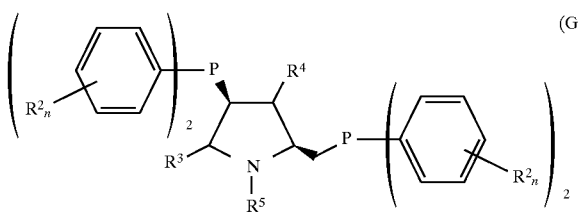

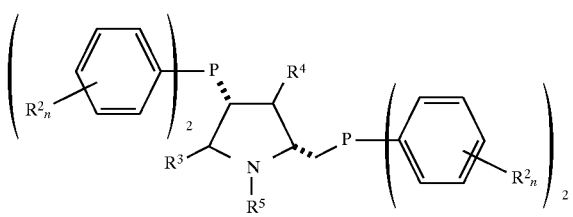

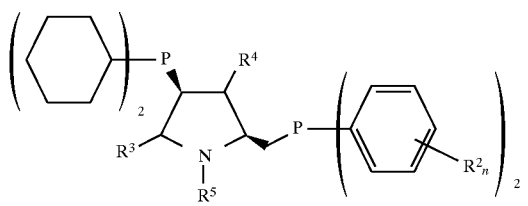

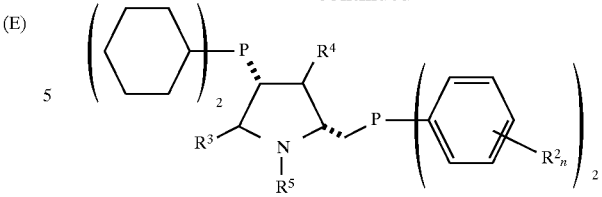

The example of the optically active bidentate phosphine ligand includes N,N-dimethyl-1-[1',2-bis(diphenylphosphino)-ferrocenyl]-ethylamine, 1-[1',2-bis(diphenylphosphino)ferrocenyl]ethanol, 1-[1,2-bis(diphenylphosphino)ferrocenyl]ethylacetate, 4,5-bis(diphenylphosphinomethyl)-2,2-dimethyl-1,3-dioxorane, 4,5-bis[bis(4'-methoxy-3',5'-dimethylphenyl)phosphinomethyl]-2,2-dimethyl-1,3-dioxorane, 2,2'-bis(diphenylphosphino)-1,1'-binaphthyl, 2,2'-bis[di(4-methylphenyl)phosphino]-1,1'-binaphthyl, 1,2-bis(diphenylphosphinomethyl)cyclohexane, diphenylphosphino-2-diphenylphosphinomethylpyrrolidine, 1-t-butoxycarbonyl-4-diphenylphosphino-2-diphenylphosphinomethylpyrrolidine, 1-t-butoxycarbonyl-4-dicyclohexylphosphino-2-diphenylphosphinomethylpyrrolidine, and the like. Of these, 2,2'-bis(diphenylphosphino)-1,1'-binaphthyl and 2,2'-bis[di(4-methylphenyl)phosphino]-1,1'-binaphthyl are preferable.

The silver salt includes silver trifluoromethanesulfonate, silver perchlorate, silver phosphate, silver nitrate, silver oxide, silver acetate, silver carbonate, silver tetrafluoroborate, silver hexafluorophosphate, silver sulfate, silver trifluoroacetate and silver zeolite.

The mole ratio of the palladium compound, the optically active bidentate phosphine ligand and the silver salt preferably ranges from 1:1:1 to 1:3:3, and more preferably from 1:1:1 to 1:2:2.

In further preferred embodiments, the palladium-optically active bidentate phosphine ligand complex in which the optically active bidentate phosphine ligand coordinates with the palladium compound may be used. In these cases, the mole ratio of the palladium-optically active bidentate phosphine ligand complex and the silver salt preferably ranges from 1:1 to 1:3, and more preferably from 1:2 to 1:3.

The preparation of the optically active bidentate phosphine ligand palladium complex of the present invention is preferably carried out in a solvent containing water.

In preferred embodiments, the ratio of water in the solvent containing water ranges from 1 to 100 moles to one mole of the palladium compound, and preferably from 1 to 50 moles.

The reaction solvent may be a solvent which does not affect the reaction and normally includes hydrocarbons such as benzene, toluene, hexane and the like, ethers such as tetrahydrofuran, diethyl ether, 1,4-dioxan and the like, amides such as formamide, N,N-dimethylformamide, N,N-dimethylacetamide, N-methylpyrrolidone, hexamethylphosphotriamide and the like, alcohols such as methanol, ethanol, propanol and the like, halogens such as chloroform, methylene chloride, ethylene dichloride and the like, ketones such as acetone, methyl ethyl ketone, methyl-i-butyl ketone and the like, acetonitrile, propionitrile, dimethylsulfoxide, water, and the like, and, a mixed solvent of them. Ketones such as acetone, methyl ethyl ketone, methyl-i-butyl ketone and the like, acetonitrile and propionitrile are preferable.

The reaction temperature normally ranges from −100° C. to the reflux temperature of the reaction solvent used, and preferably from −30° C. to 50° C.

PREPARATION 2

Instead of the palladium compound and the optically active bidentate phosphine ligand complex, the palladium-optically active bidentate phosphine ligand complex may be used.

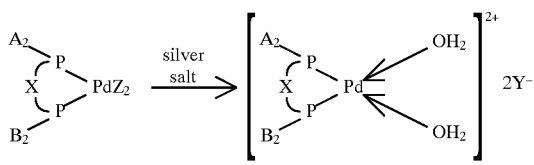

(wherein, A, B and X have the same meanings as defined above, Z represents $OSO_2CF_3$ or halogen atom.

The silver salt used in the preparation 1 may be used.

The mole ratio of the palladium-optically active bidentate phosphine ligand complex and the silver salt preferably ranges from 1:1 to 1:3, and more preferably from 1:2 to 1:3.

The preparation of the optically active bidentate phosphine ligand palladium complex of the present invention is preferably carried out in a solvent containing water.

In preferred embodiments, the ratio of water in the solvent containing water ranges from 1 to 100 moles to one mole of the palladium compound, and preferably from 1 to 50 moles.

The reaction solvent and the reaction temperature are as described in the PREPARATION 1.

The preparation of the optically active β-hydroxyketone of the present invention is further described.

The aldehyde represented by the formula (III) is allowed to react with the silyl enol ether of the formula (IV) in the presence of the catalyst comprising the optically active bidentate phosphine ligand palladium complex.

In preferred embodiments, the mole ratio of the aldehyde of (III) and the silyl enol ether of (IV) ranges from 1:0.3 to 1:3, preferably from 1:0.5 to 1:2, and more prefarably from 1:1 to 1:2.

The reaction solvent may be a solvent which does not affect the reaction, and normally includes hydrocarbons such as benzene, toluene, hexane and the like, ethers such as tetrahydrofuran, diethyl ether, 1,4-dioxan and the like, amides such as formamide, N,N-dimethylformamide, N,N-dimethylacetamide, N-methylpyrrolidone, hexamethylphosphotriamide and the like, alcohols such as methanol, ethanol, propanol and the like, halogens such as chloroform, methylene chloride, ethylene dichloride and the like, acetonitrile, dimethylsulfoxide, water, and the like, and, a mixed solvent of them. Of these, amides such as N,N-dimethylformamide, N,N-dimethylacetamide, N-methylpyrrolidone, hexamethylphosphotriamide and the like are preferable.

This reaction may be performed in either an anhydrous solvent or a solvent containing water, and preferably in a solvent containing water.

In preferred embodiments, the ratio of water in the solvent containing water ranges from 0.1 to 50 moles to one mole of the aldehyde of (III), and preferably from 0.5 to 10 moles.

The amount of the optically active bidentate phosphine ligand palladium complex which is used as the catalyst of the present reaction ranges from 0.1 to 50 mole % to the aldehyde of (III), preferably from 0.5 to 30 mole %, and more preferably from 1 to 20 mole %.

The temperature in the present reaction ranges from −100° C. to 80° C., and preferably from −40° C. to 30° C.

The present reaction yields the single compound of (V) in which $R^{15}$ is a hydrogen or a substituted silyl group, or the mixture of these compounds depending upon the reaction conditions. The compound of (V) of which $R^{15}$ is a substituted silyl group may be converted into the compound of (V) in which $R^{15}$ is hydrogen atom by eliminating the protecting group with hydrochloric acid, hydrofluoric acid or tetrabutylammonium fluoride.

The optically active bidentate phosphine ligand palladium complex which is the catalyst of the present reaction may be generated in the reaction system and used for the use of the present invention without isolating.

BEST MODE FOR CARRYING OUT THE INVENTION

The following examples are given to describe the present invention. The optical purity was determined by liquid chromatography (HPLC) analysis (Daicel Chemical Industries, Ltd., CHIRALCEL OJ).

REFERENTIAL EXAMPLE

Synthesis of (R)−(+)-2,2'-bis(diphenylphosphino)-1,1'-binaphthylpalladium dichloride (see Ozawa, F.; Kubo, A.; Matsumoto, Y.; Hayashi, T., *Organometallics* 1993, 12, 4188).

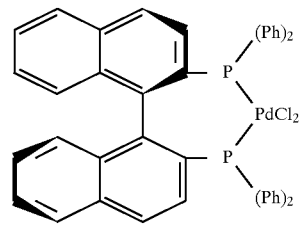

To a suspension of dichlorobis(acetonitrile)palladium (259 mg, 1 mmol) in benzene (4 ml) was added a solution of (R)−(+)-2,2'-bis(diphenylphosphino)-1,1'-binaphthylpalladium (622 mg, 1 mmol) in benzene (5 ml), and the resulting solution was stirred at room temperature for 16 hours. The reaction mixture was filtered, and then the crystals were washed with benzene (5 ml) and dried to obtain the intended product as yellow crystals (630 mg).

EXAMPLE 1

Synthesis of Palladium, di-μ-hydroxy[(R)-2,2'-bis(diphenylphosphino)-1,1'-binaphthyl]-bistetrafluoroborate

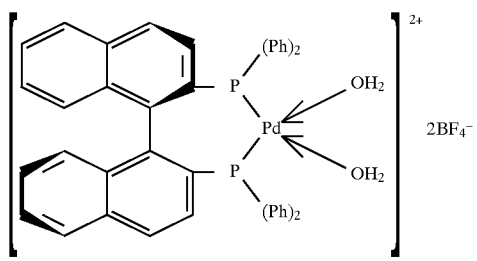

To a solution of (R)−(+)-2,2-bis(diphenylphosphino)-1,1'-binaphthylpalladium dichloride (210.0 mg, 0.262 mmol) prepared in the REFERENTIAL EXAMPLE in acetone (8 ml) and distilled water (45 g 1) was added the acetone solution (6 ml) of silver tetrafluoroborate (102.0 mg, 0.524 mmol), and the resulting solution was stirred at room temperature for 40 minutes and allowed to stand for 10 minutes. The isolated silver salt was removed by filtration, and the filtrate was concentrated to give an orange oily substance. This oily substance was crystallized from methylene chloride/diethyl ether to obtain the intended product (127.2 mg) as orange crystals.

¹HNMR (500 MHz): δ (CDCl₃) 2.30–3.22 (brs), 6.70 (2H, d, J=10.5 Hz), 6.77–6.97 (2H, m), 6.98–7.06 (2H, m), 7.19 (2H, t, J=9.2 Hz), 7.38–7.92 (24H, m);
Melting Point: coloration at 140° C., decomposition at 233°–234° C.
IR: 3450 cm⁻¹.

EXAMPLE 2

Synthesis of (3R)-trimethylsilyloxy-1,3-diphenyl-1-propanone

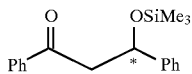

A complex prepared in the EXAMPLE 1 (149 mg, 0.10 mmol), was added to the dimethylformamide containing 1.8% of water (8 ml) at room temperature, then, benzaldehyde (0.410 ml, 4.0 mmol) and 1-phenyl-1-(trimethylsilyloxy)ethylene (1.23 ml, 6.0 mmol) were added, and the resulting mixture was stirred at room temperature for 2 hours. The reaction mixture was diluted with ether, filtered with a silica gel column, and concentrated to give a yellow oily substance. The substance was further purified by silica gel column chromatography (hexane:diethyl ether=15:1) to obtain the silyl compound (1.14, yield 95%) as a colorless oily substance. The excess ratio of enantiomer was 72% by high performance liquid chromatography.

Silyl Compound:
¹HNMR (270 MHz): δ (CDCl₃) –0.04 (9H, s), 3.02 (1H, dd, J=15.5, 4.0 Hz), 3.56 (1H, dd, J=15.5, 8.8 Hz), 5.38 (1H, dd, J=8.8, 4.0 Hz), 7.21–7.59 (8H, m), 7.92–8.02 (2H, m).

EXAMPLE 3

Synthesis of (3R)-trimethylsilyloxy-1,3-diphenyl-1-propanone and (3R)-hydroxy-1,3-diphenyl-1-propanone

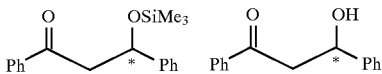

(R)-(+)-2,2'-Bis(diphenylphosphino)-1,1'-binaphthylpalladium dichloride (160 mg, 0.20 mmol) prepared in the REFERENTIAL EXAMPLE, silver trifluoromethanesulfonate (51 mg, 0.20 mmol) and Molecular Sieves 4A (1.2 g) were added to the dimethylformamide containing 1.8% of water (8 ml) at room temperature, and the resulting mixture was stirred for 20 minutes. The reaction mixture was filtered, then, benzaldehyde (0.410 ml, 4.0 mmol) and 1-phenyl-1-(trimethylsilyloxy)ethylene (1.23 ml, 6.0 mmol) were added to the filtrate, and the resulting mixture was stirred at room temperature for 13 hours. The reaction mixture was diluted with ether, filtered with a silica gel column, and concentrated to give a yellow oily substance. The substance was further purified by silica gel column chromatography (hexane:diethyl ether=2:1) to obtain the silyl compound (1.04 g, yield 87%) and the hydroxyl compound (82 mg, yield 9%) as colorless oily substances. The excess ratios of enantiomer were 71% and 73%, respectively, by high precision liquid chromatography.

The spectrum data of the silyl compound obtained agreed with those in the EXAMPLE 2.

Hydroxyl Compound:
¹HNMR (270 MHz): δ (CDCl₃) 3.38 (2H, d, J=6.0 Hz), 3.60 (1H, d, J=3.0 Hz), 5.35 (1H, dt, J=6.0, 3.0 Hz), 7.24–7.51 (7H, m), 7.54–7.63 (1H, m), 7.91–8.00 (2H, m).

EXAMPLE 4

Synthesis of (3R)-hydroxy-1,5-diphenyl-1-pentanone

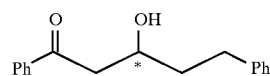

A complex prepared in the EXAMPLE 1 (149 mg, 0.10 mmol) was added to a dimethylformamide containing 1.8% of water (8 ml) at room temperature, then, hydrocinnamaldehyde (0.53 ml, 4.0 mmol) and 1-phenyl-1-(trimethylsilyloxy)ethylene (1.23 ml, 6.0 mmol) were added, and the resulting mixture was stirred at room temperature for 5 hours. The reaction mixture was diluted with ether, filtered with a short silica gel column, and concentrated to give a yellow oily substance. To the oily substance, 20 ml of tetrahydrofuran and 10 ml of 1N hydrochloric acid were added, and the resulting mixture was stirred at room temperature for 30 minutes. The mixture was extracted with diethyl ether three times, and the ether layers were combined, washed with saturated sodium hydrogencarbonate, water and a saturated sodium chloride solution, and dried over sodium sulfate. The solvent was evaporated and the residue was purified by silica gel chromatography (hexane:diethyl ether=2:1) to obtain the intended product (934 mg, yield 92%) as a colorless oily substance. The excess ratio of enantiomer was 73%.

¹HNMR (270 MHz): δ (CDCl₃) 1.73–2.04 (2H, m), 2.68–2.97 (2H, m), 3.06 (1H, dd, J=18.0, 8.5 Hz), 3.17 (1H, dd, J=18.0, 3.2 Hz), 3.36 (1H, brd, J=3.2 Hz), 4.17–4.31 (1H, m), 7.14–7.34 (5H, m), 7.42–7.52 (2H, m), 7.54–7.63 (1H, m), 7.89–7.99 (2H, m).

EXAMPLE 5

Synthesis of (3R)-hydroxy-1,5-diphenyl-1-pentanone

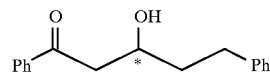

(R)-(+)-2,2'-Bis(diphenylphosphino)-1,1'-binaphthylpalladium dichloride (160 mg, 0.20 mmol), silver trifluoromethanesulfonate (51 mg, 0.20 mmol) and Molecular Sieves 4A (1.2 g) were added to the dimethylformamide containing 1.8% of water (8 ml) at room temperature, and the resulting mixture was stirred for 20 minutes. The reaction mixture was filtered, then, hydrocinnamaldehyde (0.53 ml, 4.0 mmol) and 1-phenyl-1-(trimethylsilyloxy)ethylene (1.23 ml, 6.0 mmol) were added to the filtrate, and the resulting mixture was stirred at room temperature for 38 hours. The reaction mixture was diluted with ether, filtered with a short silica gel column, and concentrated to give a yellow oily substance. To the oily substance, 20 ml of tetrahydrofuran and 10 ml of 1N hydrochloric acid were added, and the resulting mixture was stirred at room temperature for 30 minutes. The mixture was extracted with diethyl ether three times, and the ether layers were combined, washed with saturated sodium hydrogencarbonate, water and a saturated sodium chloride solution, and dried over sodium sulfate. The solvent was evaporated and the residue was purified by silica gel chromatography (hexane:diethyl ether=2:1) to obtain the intended product (the hydroxyl compound) (873 mg, yield 86%) as a colorless oily substance. The excess ratio of enantiomer was 73%. The spectrum data of the substance obtained agreed with those of the substance obtained in the EXAMPLE 4.

EXAMPLE 6

Synthesis of (R*,R*)-2-(hydroxyphenylmethyl)cyclohexanone and (R*,S*)-2-(hydroxyphenylmethyl)cyclohexanone

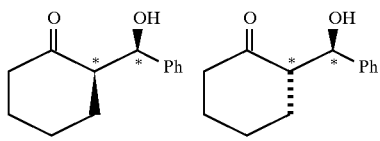

The complex prepared in the EXAMPLE 1 (149 mg, 0.10 mmol) was added to the dimethylformamide containing 1.8% of water (8 ml) at room temperature, then, benzaldehyde (0.41 ml, 4.0 mmol) and 1-(trimethylsilyloxy)-1-cyclohexene (1.20 ml, 6.0 mmol) were added, and the resulting mixture was stirred at room temperature for 10 hours. The reaction mixture was diluted with ether, filtered with a short silica gel column, and concentrated to give a yellow oily substance. To the oily substance, 20 ml of tetrahydrofuran and 10 ml of 1N hydrochloric acid were added, and the resulting mixture was stirred at room temperature for 30 minutes. The mixture was extracted with diethyl ether three times, and the ether layers were combined, washed with saturated sodium hydrogencarbonate, water and a saturated sodium chloride solution, and dried over sodium sulfate. The solvent was evaporated and the residue was purified by silica gel chromatography (hexane:diethyl ether=2:1) to obtain the syn-form (349 mg, yield 43%) and the anti-form (123 mg, yield 15%) as colorless oily substances. The excess ratio of enantiomer of the main product, the syn-form, was 73%.

Syn-form $^1$HNMR (270 MHz): δ (CDCl$_8$) 1.41–1.91 (5H, m), 2.02–2.15 (1H, m), 2.29–2.52 (2H, m), 2.54–2.66 (1H, m), 3.02 (1H, d, J=3.0 Hz), 3.59 (1H, brs), 7.20–7.39 (5H, m);

Anti-form $^1$HNMR (270 MHz): δ (CDCl$_3$) 1.21–1.40 (1H, m), 1.42–1.85 (4H, m), 2.02–2.16 (1H, m), 2.28–2.69 (3H, m), 3.96 (1H, brd, J=2.2 Hz), 4.79 (1H, dd, J=9.0, 2.2 Hz), 7.23–7.40 (5H, m).

EXAMPLE 7

Synthesis of (R*,R*)-2-(hydroxyphenylmethyl)cyclohexanone and (R*,S*)-2-(hydroxyphenylmethyl)cyclohexanone

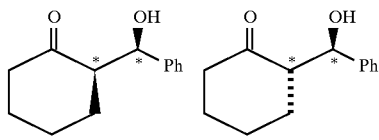

(R)-(+)-2,2'-Bis(diphenylphosphino)-1,1'-binaphthylpalladium dichloride (160 mg, 0.20 mmol), silver trifluoromethanesulfonate (51 mg, 0.20 mmol) and Molecular Sieves 4A (1.2 g) were added to the dimethylformamide containing 1.8% of water (8 ml) at room temperature, and the resulting mixture was stirred for 20 minutes. The reaction mixture was filtered, then, benzaldehyde (0.41 ml, 4.0 mmol) and 1-(trimethylsilyloxy)-1-cyclohexene (1.20 ml, 6.0 mmol) were added to the filtrate, and the resulting mixture was stirred at room temperature for 109 hours. The reaction mixture was diluted with ether, filtered with a short silica gel column, and concentrated to give a yellow oily substance. To the oily substance, 20 ml of tetrahydrofuran and 10 ml of 1N hydrochloric acid were added, and the resulting mixture was stirred at room temperature for 30 minutes. The mixture was extracted with diethyl ether three times, and the ether layers were combined, washed with saturated sodium hydrogencarbonate, water and a saturated sodium chloride solution, and dried over sodium sulfate. The solvent was evaporated and the residue was purified by silica gel chromatography (hexane:diethyl ether=2:1) to give the syn-form (349 mg, yield 43%) and the anti-form (123 mg, yield 15%) as colorless oily substances. The spectrum data of the substances obtained agreed with those of the substances obtained in the EXAMPLE 6.

EFFECTS OF THE INVENTION

The present invention provides a novel optically active bidentate phosphine ligand palladium complex and a method of preparing optically active β-hydroxyketones by using the complex to obtain the intended products in remarkably excellent asymmetric yields compared with those in the prior art.

What is claimed is:

1. An optically active bidentate phosphine ligand palladium complex which is prepared from a palladium compound, an optically active bidentate phosphine ligand and silver salt, or from a palladium-optically active bidentate phosphine ligand complex and silver salt.

2. An optically active bidentate phosphine ligand palladium complex of the formula (I) or (II):

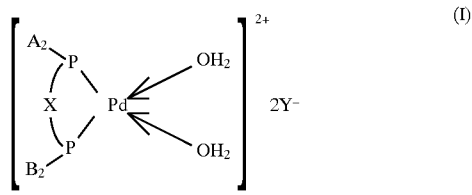

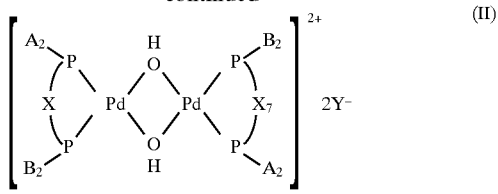

[wherein Y⁻ represents an anion pair which may form salt; X represents

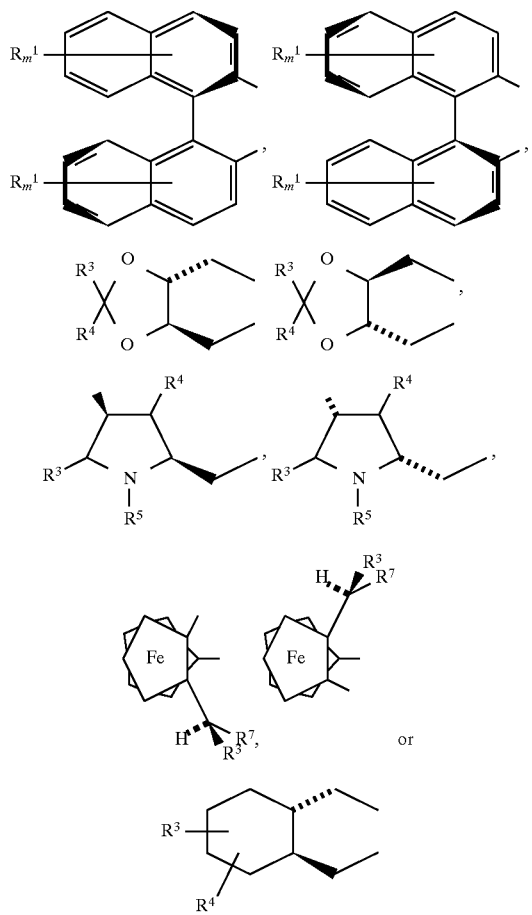

{where $R^1$ represents hydrogen atom, $C_{1-6}$ alkyl group, $C_{2-6}$ alkenyl group, $C_{2-6}$ alkynyl group, $C_{1-6}$ alkoxyl group (said alkyl group, alkenyl group, alkynyl group and alkoxyl group each is unsubstituted or substituted by halogen atom, hydroxyl group, tri($C_{1-6}$ alkyl)silyl group, $C_{1-6}$ alkyldiphenylsilyl group, di($C_{1-6}$ alkyl)phenylsilyl group, $C_{1-6}$ alkoxyl group, $C_{6-10}$ aromatic group or heterocyclic group), cyano group, nitro group, halogen atom or phenyl group (said phenyl group is unsubstituted or substituted by $C_{1-6}$ alkyl group, $C_{1-6}$ alkoxyl group, cyano group, nitro group or halogen atom);

$R^3$ and $R^4$ each independently represents $C_{1-6}$ alkyl group;

$R^5$ represents hydrogen atom, $COR^6$, $CO_2R^6$ or $CONHR^6$ ($R^6$ represents $C_{1-6}$ alkyl group);

$R^7$ represents hydroxyl group, $NR^4{}_2$ or $OCOR^4$;

m represents 1 or 2; when m is 2, two $R^1$s may be same or different}; and

A and B each independently represents phenyl group or cyclohexyl group (said phenyl group and cyclohexyl group are unsubstituted or substituted by $R^2$ ($R^2$ has the same meaning as defined in $R^1$))].

3. The optically active bidentate phosphine ligand palladium complex which is prepared from a palladium compound, an optically active bidentate phosphine ligand and silver salt, or from a palladium-optically active bidentate phosphine ligand complex and silver salt as claimed in claim 2.

4. The optically active bidentate phosphine ligand palladium complex of the formula (I) or (II) as claimed in claim 2, wherein Y⁻ represents $ClO_4^-$, $NO_3^-$, $CH_3COO^-$, $CF_3SO_3^-$, $BF_4^-$, $PF_6^-$, $CF_3CO_2^-$, $AgCO_3^-$ or $AgPO_4^-$.

5. The optically active bidentate phosphine ligand palladium complex as claimed in claim 4, wherein $R^1$ and, $R^2$ each independently represents hydrogen atom, $C_{1-6}$ alkyl group, $C_{2-6}$ alkynyl group, $C_{1-6}$ alkoxyl group (said alkyl group, alkynyl group and alkoxyl group each is unsubstituted or substituted by halogen atom, tri($C_{1-6}$ alkyl)silyl group, $C_{1-6}$ alkyldiphenylsilyl group, di($C_{1-6}$ alkyl)phenylsilyl group, $C_{1-6}$ alkoxyl group, $C_{6-10}$ aromatic group or heterocyclic group), cyano group, halogen atom or phenyl group (said phenyl group is unsubstituted or substituted by $C_{1-6}$ alkyl group, $C_{1-6}$ alkoxyl group, cyano group or halogen atom).

6. The optically active bidentate phosphine ligand palladium complex as claimed in claim 5, wherein $R^1$ represents hydrogen atom.

7. The optically active bidentate phosphine ligand palladium complex as claimed in claim 6, wherein X represents

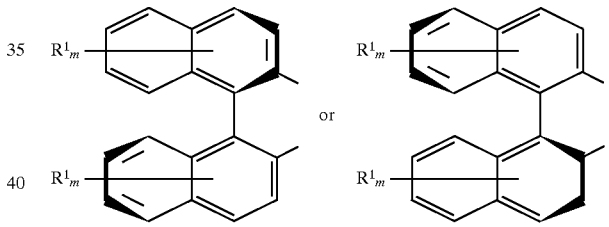

8. The optically active bidentate phosphine ligand palladium complex as claimed in claim 7, wherein Y⁻ represents $ClO_4^-$, $CF_3SO_3^-$, $BF_4^-$ or $PF_6^-$.

9. The optically active bidentate phosphine ligand palladium complex as claimed in claim 8, wherein $R^2$ represents hydrogen atom or $C_{1-6}$ alkyl group.

10. The optically active bidentate phosphine ligand palladium complex as claimed in claim 9, wherein $R^2$ represents hydrogen atom or $C_{1-6}$ alkyl group and the number of $R^2$ is 3.

11. The optically active bidentate phosphine ligand palladium complex as claimed in claim 10, wherein $R^2$ represents hydrogen atom, methyl group or methoxy group and the number of $R^2$ is 1.

12. The optically active bidentate phosphine ligand palladium complex as claimed in claim 11, wherein $R^2$ represents methyl group or methoxy group, the number of $R^2$ is 1, and Y⁻ represents $BF_1^-$.

13. The optically active bidentate phosphine ligand palladium complex as claimed in claim 11, wherein $R^2$ represents a hydrogen atom and Y⁻ represents $BF_4^-$.

14. A method of preparating an optically active β-hydroxyketones of the formula (V):

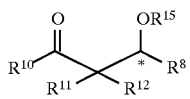

(V)

[wherein $R^8$ represents $C_{1-10}$ alkyl group, $C_{3-10}$ cycloalkyl group, $C_{2-10}$ alkenyl group, $C_{2-10}$ alkynyl group {said alkyl group, cycloalkyl group, alkenyl group and alkynyl group each is unsubstituted or substituted by halogen atom, hydroxyl group, $C_{1-10}$ alkoxyl group, $NR^{13}R^{13'}$ ($R^{13}$ and $R^{13'}$ each independently represents hydrogen atom, $C_{1-10}$ alkyl group or $C_{6-10}$ aromatic group), $SR^{14}$ ($R^{14}$ has the same meaning as definend in $R^{13}$), $C_{6-10}$ aromatic group or heterocyclic group}, $C_{6-10}$ aromatic group or heterocyclic group (said aromatic group and heterocyclic group each optionally has one to three and same or different substituents selected from the group consisting of $C_{1-10}$ alkyl group, $C_{1-10}$ alkoxyl group, halogen atom, nitro group, hydroxyl group, cyano group, $C_{1-10}$ alkoxycarbonyl group, $C_{1-10}$ alkanoyl group, amino group, N-mono($C_{1-10}$ alkyl)amino group, N,N-di($C_{1-10}$ alkyl)-amino group, carbamoyl group, N-mono($C_{1-10}$ alkyl)carbamoyl group, N,N-di($C_{1-10}$ alkyl) carbamoyl group, amino($C_{1-10}$ alkyl) group, N-mono($C_{1-10}$ alkyl)amino($C_{1-10}$ alkyl) group and N,N-di($C_{1-10}$ alkyl) amino($C_{1-10}$ alkyl) group);

$R^{10}$ and $R^{11}$ each independently represents hydrogen atom, $C_{1-10}$ alkyl group, $C_{1-10}$ alkoxyl group, $C_{1-10}$ thioalkoxyl group, $C_{3-10}$ cycloalkyl group, $C_{2-10}$ alkenyl group, $C_{2-10}$ alkynyl group {said alkyl group, alkoxyl group, thioalkoxyl group, cycloalkyl group, alkenyl group and alkynyl group is unsubstituted or substituted by halogen atom, hydroxyl group, $C_{1-10}$ alkoxyl group, $NR^{13}R^{13'}$ ($R^{13}$ and $R^{13'}$ each independently represents as defined above), $SR^{14}$ ($R^{14}$ has the meaning as defined above), $C_{6-10}$ aromatic group or heterocyclic group}, $C_{6-10}$ aromatic group or heterocyclic group (said aromatic group and heterocyclic group each optionally has one to three and same or different substituents selected from the group consisting of $C_{1-10}$ alkyl group, $C_{1-10}$ alkoxyl group, halogen atom, nitro group, hydroxyl group, cyano group, $C_{1-10}$ alkoxycarbonyl group, $C_{1-10}$ alkanoyl group, amino group, N-mono($C_{1-10}$ alkyl)amino group, N,N-di($C_{1-10}$ alkyl)amino group, carbamoyl group, N-mono($C_{1-10}$ alkyl)carbamoyl group, N,N-di($C_{1-10}$ alkyl)carbamoyl group, amino($C_{1-10}$ alkyl) group, N-mono($C_{1-10}$ alkyl) amino($C_{1-10}$ alkyl) group and N,N-di($C_{1-10}$ alkyl) amino($C_{1-10}$ alkyl) group); or $R^{10}$ and $R^{11}$, together with the carbon atom to which they are bound, represent a 5 to 7 membered carbocyclic group;

$R^{12}$ represents hydrogen atom, $C_{1-10}$ alkyl group (said alkyl group is unsubstituted or substituted by halogen atom, hydroxyl group or $C_{1-10}$ alkoxyl group); and $R^{15}$ represents hydrogen atom or substituted silyl group ], comprising of reacting aldehyde of the formula (III):

(III)

with silyl enol ether of the formula (IV):

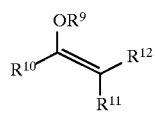

(IV)

in the presence of the complex as claimed in claim 1.

15. The method of preparating an optically active β-hydroxyketones as claimed in claim 14, wherein $R^8$ represents $C_{1-10}$ alkyl group, $C_{3-10}$ cycloalkyl group {said alkyl group and cycloalkyl group each is unsubstituted or substituted by halogen atom, hydroxyl group, $C_{1-10}$ alkoxyl group, $NR^{13}R^{13'}$ ($R^{13}$ and $R^{13'}$ each independently represents hydrogen atom, $C_{1-10}$ alkyl group or $C_{6-10}$ aromatic group), $SR^{14}$ ($R^{14}$ has the same meaning as defined in $R^{13}$), $C_{6-10}$ aromatic group or heterocyclic group}, $C_{6-10}$ aromatic group or heterocyclic group (said aromatic group and heterocyclic group each optionally has one to three and same or different substituents selected from the group consisting of $C_{1-10}$ alkyl group, $C_{1-10}$ alkoxyl group, halogen atom, nitro group, hydroxyl group, cyano group, $C_{1-10}$ alkoxycarbonyl group, $C_{1-10}$ alkanoyl group, amino group, N-mono($C_{1-10}$ alkyl) amino group, N,N-di($C_{1-10}$ alkyl)amino group, carbamoyl group, N-mono($C_{1-10}$ alkyl)carbamoyl group, N,N-di($C_{1-10}$ alkyl)carbamoyl group, amino($C_{1-10}$ alkyl) group, N-mono ($C_{1-10}$ alkyl)amino($C_{1-10}$ alkyl) group and N,N-di($C_{1-10}$ alkyl)amino($C_{1-10}$ alkyl) group).

16. The method of preparing the optically active β-hydroxyketones as claimed in claim 15, wherein $R^{10}$ and $R^{11}$ each independently represents hydrogen atom, $C_{1-10}$ alkyl group, $C_{1-10}$ alkoxyl group, $C_{1-10}$ thioalkoxyl group, $C_{3-10}$ cycloalkyl group {said alkyl group, alkoxyl group, thioalkoxyl group and cycloalkyl group each is unsubstituted or substituted by halogen atom, hydroxyl group, $C_{1-10}$ alkoxyl group, $NR^{13}R^{13'}$ ($R^{13}$ and $R^{13'}$ each independently represents hydrogen atom, $C_{1-10}$ alkyl group or $C_{6-10}$ aromatic group), $SR^{14}$ ($R^{14}$ has the same meaning as defined in $R^{13}$), $C_{6-10}$ aromatic group or heterocyclic group}, $C_{6-10}$ aromatic group or heterocyclic group (said aromatic group and heterocyclic group each optionally has one to three and same or different substituents selected from the group consisting of $C_{1-10}$ alkyl group, $C_{1-10}$ alkoxyl group, halogen atom, nitro group, hydroxyl group, cyano group, $C_{1-10}$ alkoxycarbonyl group, $C_{1-10}$ alkanoyl group, amino group, N-mono($C_{1-10}$ alkyl)amino group, N,N-di($C_{1-10}$ alkyl) amino group, carbamoyl group, N-mono($C_{1-10}$ alkyl) carbamoyl group, N,N-di($C_{1-10}$ alkyl)carbamoyl group, amino($C_{1-10}$ alkyl) group, N-mono($C_{1-10}$ alkyl)amino($C_{1-10}$ alkyl) group and N,N-di($C_{1-10}$ alkyl)amino($C_{1-10}$ alkyl) group); or $R^{10}$ and $R^{11}$, together with the carbon atom to which they are bound, represent a 5 to 7 membered carbocyclic group.

17. The method of preparing the optically active δ-hydroxyketones as claimed in claim 16, wherein $R^9$ represents trimethylsilyl group, triethylsilyl group, t-butyldimethylsilyl group or t-butyldipheylsilyl group.

18. The method of preparing the optically active β-hydroxyketones as claimed in claim 14, wherein the palladium-optically active bidentate phosphine ligand complex is an optically active-2,2'-bis(diphenylphosphino)-1,1'-binaphthyl palladium of the formula (4):

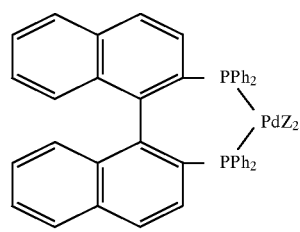

(4)

(wherein Z represents $OSO_2CF_3$ or halogen atom).

* * * * *